(12) United States Patent
Grogan et al.

(10) Patent No.: US 9,051,549 B2
(45) Date of Patent: Jun. 9, 2015

(54) IN SITU TISSUE ENGINEERING USING MAGNETICALLY GUIDED THREE DIMENSIONAL CELL PATTERNING

(75) Inventors: Shawn Patrick Grogan, Oceanside, CA (US); Darryl David D'Lima, San Diego, CA (US); Clifford W. Colwell, Jr., La Jolla, CA (US); Sungho Jin, San Diego, CA (US)

(73) Assignee: Scripps Health, San Diego, CA (US)

( * ) Notice: Subject to any disclaimer, the term of this patent is extended or adjusted under 35 U.S.C. 154(b) by 271 days.

(21) Appl. No.: 13/402,627

(22) Filed: Feb. 22, 2012

(65) Prior Publication Data

US 2012/0214217 A1    Aug. 23, 2012

Related U.S. Application Data

(60) Provisional application No. 61/445,403, filed on Feb. 22, 2011.

(51) Int. Cl.
*C12N 5/077* (2010.01)
*A61K 35/00* (2006.01)
*A61K 35/12* (2006.01)

(52) U.S. Cl.
CPC ............. *C12N 5/0655* (2013.01); *A61K 35/12* (2013.01); *C12N 2529/00* (2013.01); *C12N 2533/10* (2013.01); *C12N 2533/74* (2013.01)

(58) Field of Classification Search
None
See application file for complete search history.

(56) References Cited

PUBLICATIONS

Fu, C-Y et al "A Simple Cell Patterning Method Using Magnetic Particle-Containing Photosensitive Poly (Ethylene Glycol) Hydrogel Blocks: A Technical Note" Tissue Engineering: Part C, May 19, 2011, 17(8), 871-877. (DOI: 10.1089/ten.tec.2010.0690).*
Grogan et al "In Situ Tissue Engineering Using Magnetically Guided Three-Dimensional Cell Patterning" Tissue Engineering: Part C, Feb. 10, 2012, 18(7), pp. 496-506. (DOI: 10.1089/ten.tec.2011.0525).*
Akeda et al. (2006). Platelet-rich plasma stimulates porcine articular chondrocyte proliferation and matrix biosynthesis. Osteoarthritis Cartilage 14, pp. 1272-1280.
Alsberg et al. (2003). Regulating bone formation via controlled scaffold degradation. J. Dent. Res. 82:903-908.
Arbab et al. (2004). In vivo trafficking and targeted delivery of magnetically labeled stem cells. Hum Gene Ther. 15:351-360.
Bouhadir et al. (2001). Degradation of partially oxidized alginate and its potential application for tissue engineering. Biotech. Prog. 17:945-950.

(Continued)

*Primary Examiner* — Rosanne Kosson
*Assistant Examiner* — Aaron J Kosar
(74) *Attorney, Agent, or Firm* — Wilson Sonsini Goodrich & Rosati

(57) ABSTRACT

Methods are provided for the three dimensional manipulation of cells, and for the formation of an organized engineered cell tissue. Also provided are the organized engineered cell tissues produced by the methods. In one method, a plurality of magnetically labeled cells are mixed with a cross-linkable hydrogel to form a cell-hydrogel mixture, the at least a portion of the plurality of magnetically labeled cells are manipulated with a magnetic field to arrange the magnetically labeled cells into a specific cellular arrangement, and the hydrogel is crosslinked to form the organized engineered cell tissue. The approach presented herein offers a means to circumvent the deficiencies in the field of regenerative medicine, and allows for the production of organized tissues in situ with specific cellular organizations that mimic the native tissue.

45 Claims, 24 Drawing Sheets

(56) References Cited

PUBLICATIONS

Bryant et al. (2004). Synthesis and characterization of photopolymerized multifunctional hydrogels: water-soluble poly(vinyl alcohol) and chondroitin sulfate macromers for chondrocyte encapsulation. Macromolecules 37:6726-6733.

Chen et al. (1999). Functions of hyaluronan in wound repair. Wound Rep. Reg. 7:79-89.

Di Martino et al. (2005). Chitosan: a versatile biopolymer for orthopaedic tissue-engineering. Biomaterials 26:5983-5990.

Frasca et al. (2009). Formation of a three-dimensional multicellular assembly using magnetic patterning. Langmuir 25:2348-2354.

Gaissmaier et al. (2005). Effect of human platelet supernatant on proliferation and matrix synthesis of human articular chondrocytes in monolayer and three-dimensional alginate cultures. Biomaterials 26:1953-1960.

Grogan et al. (2009). Mesenchymal progenitor cell markers in human articular cartilage: normal distribution and changes in osteoarthritis . . . Arthritis Res. Ther. 11:R85.

Henning et al. (2008). Labeling hESCs and hMSCs with iron oxide nanoparticles for non-invasive in vivo tracking with MR imaging. J Vis. Exp. 13:685-686.

Huang et al. (2011). Biomimetic properties of an injectable chitosan/nano-hydroxyapatite/collagen composite. Materials Science and Engineering: C. 31:683-687.

Ito et al. (2007). Magnetic force-based cell patterning using Arg-Gly-Asp (RGD) peptide-conjugated magnetite cationic liposomes. J. Biosci. Bioeng. 104:288-293.

Khor et al. (2003). Implantable applications of chitin and chitosan. Biomaterials 24:2339-2349.

Kim et al. (2003). Experimental model for cartilage tissue engineering to regenerate the zonal organization of articular cartilage. Osteoarthritis Cartilage 11:653-664.

Kitagawa et al. (1997). Mechanical properties of dragline and capture thread for the spider *Nephila clavata*. J. Mater. Sci. 32:2005-2012.

Klein et al. (2003). Tissue engineering of stratified articular cartilage from chondrocyte subpopulations. Osteoarthritis Cartilage 11:595-602.

Klein et al. (2009). Tissue engineering of articular cartilage with biomimetic zones. Tissue Eng. Part B Rev. 15:143-157.

Kong et al. (2004). Controlling degradation of hydrogels via the size of crosslinked junctions. Adv Mater 16:1917-1921.

Lahiji et al. (2000). Chitosan supports the expression of extracellular matrix proteins in human osteoblasts and chondrocytes. J. Biomed. Mater. Res. 51: 586-595.

Lee et al. (2007). Integration of layered chondrocyte-seeded alginate hydrogel scaffolds. Biomaterials 28:2987-2993.

Lee et al. (2008). An injectable enzymatically crosslinked hyaluronic acid-tyramine hydrogel system with independent tuning of mechanical strength and gelation rate. Softmatter. 4:880-887.

Li et al. (2004). Photocrosslinkable polysaccharides based on chondroitin sulfate. J. Biomed. Mater. Res. A 68:28-33.

Lin et al. (2008). Magnetic reconstruction of three-dimensional tissues from multicellular spheroids. Tissue Eng. Part C Methods 14:197-205.

Muzzarelli et al. (1994). Stimulatory effect on bone formation exerted by a modified chitosan. Biomaterials 15:1075-1081.

Noth et al. (2010). Cell delivery therapeutics for musculoskeletal regeneration. Advanced Drug Delivery Reviews 62:765-783.

Obradovic et al. (2001). Integration of engineered cartilage. J. Orthop. Res. 19:1089-1097.

Pieper et al. (1999). Preparation and characterization of porous crosslinked collagenous matrices containing bioavailable chondroitin sulphate. Biomaterials 20:847-858.

Roberts et al. (2009) Immunohistochemical study of collagen types I and II and procollagen IIA in human cartilage repair tissue following autologous chondrocyte implantation. Knee 16:398-404.

Sellmyer et al. (2006). Appendix to Advanced Magnetic Nanostructures, Springer Science, pp. 491-496.

Sharma et al. (2007). Designing zonal organization into tissue-engineered cartilage. Tissue Eng. 13:405-414.

Shimizu et al. (2006). Enhanced cell-seeding into 3D porous scaffolds by use of magnetite nanoparticles. J. Biomed. Mater. Res. B Appl. Biomater. 77:265-272.

Shimizu et al. (2007). Bone tissue engineering with human mesenchymal stem cell sheets constructed using magnetite nanoparticles and magnetic force. J. Biomed. Mater. Res. B Appl. Biomater. 82:471-480.

Simmons et al. (2004). Dual growth factor delivery and controlled scaffold degradation enhance in vivo bone formation by transplanted bone marrow stromal cells. Bone 35:562-569.

Steinert et al. (2003). Chondrogenic differentiation of mesenchymal progenitor cells encapsulated in ultrahigh-viscosity alginate. J. Orthop. Res. 21, pp. 1090-1097.

Taguchi et al. (2002). Swelling behavior of hyaluronic acid and type II collagen hydrogels prepared by using conventional crosslinking and subsequent additional polymer interactions. J. Biomater. Sci Polym. Ed. 13:43-52.

Tallheden et al. (2006). In vivo MR imaging of magnetically labeled human embryonic stem cells. Life Sci. 79:999-1006.

Varghese et al. (2006). Hydrogels for musculoskeletal tissue engineering. Adv. Polym. Sci. 203:95-144.

Vunjak-Novakovic et al. (2004). Tissue engineering of ligaments. Annu. Rev. Biomed. Eng. 6:131-156.

Woodfield et al. (2004). Design of porous scaffolds for cartilage tissue engineering using a three-dimensional fiber-deposition technique. Biomaterials 25:4149-4161.

Yamamoto et al. (2009). Preparation of artificial skeletal muscle tissues by a magnetic force-based tissue engineering technique. J. Biosci. Bioeng. 108:538-543.

Young et al. (2005). Gelatin as a delivery vehicle for the controlled release of bioactive molecules. J. Control. Release 109:256-274.

Zeifang et al. (2010). Autologous chondrocyte implantation using the original periosteum-cover technique versus matrix-associated autologous chondrocyte implantation: a randomized clinical trial. Am. J. Sports Med. 38:924-933.

\* cited by examiner

IN SITU TISSUE ENGINEERING USING MAGNETICALLY GUIDED THREE DIMENSIONAL CELL PATTERNING

CROSS REFERENCE TO RELATED APPLICATION

This application claims priority from U.S. Provisional Application Ser. No. 61/445,403, filed Feb. 22, 2011, the disclosure of which is incorporated by reference in its entirety for all purposes.

BACKGROUND OF THE INVENTION

Degeneration of tissues such as cartilage is a common health condition that has a significant economic impact and quality of life impact. For example, osteoarthritis (OA) and other rheumatic diseases are among the most common health conditions and are the number one cause of disability in the United States, affecting an estimated 27 million Americans in 2008 (Lawrence et al. (2008). Arthritis Rheum. 58, pp. 26-35). The economic impact of arthritis in the United States is estimated at $128 billion per year, representing more than 2% of the gross domestic product ((CDC), C.f.D.C.a.P. *MMWR Morb Mortal Wkly Rep.* 56, 4-7 (2007)). Only symptom-modifying therapies are used to treat OA (Roddy et al. (2005). Rheumatology (Oxford, England) 44, pp. 67-73; Zhang et al. (2005). Annals of the rheumatic diseases 64, pp. 669-681).

For two decades, one major cell-based tissue regeneration strategy—autologous cell implantation, has been clinically approved. However, this procedure does not predictably result in functional hyaline cartilage, but rather in fibrocartilage (Roberts et al. (2009). Knee 16, pp. 398-404; Zeifang et al. Am. J. Sports Med. 38, pp. 924-933), which lacks the cellular and extra-cellular matrix (ECM) organization required to support the demanding load-bearing functions of this tissue (Lee et al. (2007). Biomaterials 28, pp. 2987-2993; Klein et al. (2009). Tissue Eng. Part B Rev. 15, pp. 143-157).

Although in vitro prefabrication of tissue grafts has shown variable success in animal models and cartilage tissues engineered with zonal organization has improved to provide a natural spatial cell distribution, these approaches have not been transferred to a clinical setting (Chu et al. (2010). Tissue Eng. Part B Rev. 16, pp. 105-115; Kim et al. (2003). Osteoarthritis Cartilage 11, pp. 653-664; Klein et al. (2009). Tissue Eng. Part B Rev. 15, pp. 143-157; Klein et al. (2003). Osteoarthritis Cartilage 11, pp. 595-602; Sharma et al. (2007). Tissue Eng. 13, pp. 405-414; Woodfield et al. (2004). Biomaterials 25, pp. 4149-4161). The procedures are laborious, expensive and integration into the surrounding host cartilage tissue is an unresolved issue (Obradovic et al. (2001). J. Orthop. Res. 19, pp. 1089-1097).

Accordingly, there is a need for improved methods of tissue engineering, particularly for tissues such as cartilage. The methods of the present invention provide such improved methods.

SUMMARY OF THE INVENTION

The approach presented herein is a means to circumvent the deficiencies in the field of regenerative medicine generally, and allows for the production of organized tissues in situ with specific cellular organizations that mimic the native tissue. The creation of organized repair tissue may provide more appropriate three-dimensional cues for tissue formation. Direct implantation and organization in situ may circumvent the need for long-term in vitro culture, and may also allow for more complex tissue types to be formed. The present invention addresses this and other needs.

The present invention provides an approach for manipulation of cells in a three dimensional manner with the use of magnetic particles. The methods provided herein allow for the control of cell distance, cell density, and cell orientation within a single hydrogel without specialized "pre-functionalization" of the magnetic particles.

In one embodiment, the present invention provides a method of forming an organized engineered cell tissue. The method comprises mixing a plurality of magnetically labeled cells with a cross-linkable hydrogel to form a cell-hydrogel mixture, manipulating at least a portion of the plurality of magnetically labeled cells with a magnetic field to arrange the magnetically labeled cells into a specific cellular arrangement, and crosslinking the hydrogel, thereby forming the organized engineered cell tissue.

In another embodiment, the present invention provides a method of forming an organized engineered cell tissue. The method comprises mixing a first plurality of magnetically labeled cells with a first cross-linkable hydrogel to form a first cell-hydrogel mixture, manipulating at least a portion of the first plurality of magnetically labeled cells with a magnetic field to arrange the magnetically labeled cells into a first specific cellular arrangement, crosslinking the first cross-linkable hydrogel, thereby forming a first organized engineered cell tissue; mixing a second plurality of magnetically labeled cells with a second cross-linkable hydrogel to form a second cell-hydrogel mixture, manipulating at least a portion of the second plurality of magnetically labeled cells with a magnetic field to arrange the magnetically labeled cells into a second specific cellular arrangement, and crosslinking the second cross-linkable hydrogel, thereby forming a second organized engineered cell tissue, and combining the first and second organized engineered cell tissues. In one embodiment, the combining in step is within a tissue defect in a patient. In one embodiment, the combining step comprises fusing the two organized cell tissues together.

In one embodiment, the hydrogel used in the methods of the invention comprises a natural polymer. In a further embodiment, the natural polymer of the hydrogel is selected from hyaluronic acid, chondroitin sulfate, collagen, Matrigel™, alginate, chitosan, fibrin, agarose, silk, or combinations thereof.

In one embodiment, the hydrogel used in the methods of the invention comprises a synthetic polymer. In a further embodiment, the hydrogel comprises a synthetic polymer selected from polymers and copolymers of ethylene oxide, poly(ethylene oxide), poly(ethylene glycol diacrylate), polymers and copolymers of vinyl alcohol, poly(vinyl alcohol), polymers and copolymers of acrylic or methacrylic acid, poly (acrylic acid), poly(acrylamidomethyl propane sulfonic acid), poly(hydroxylethyl methacrylate), poly(propylene fumarate-co-ethylene glycol), or combinations thereof.

As described in detail below, when multiple hydrogels are fused together to form a multi-layer hydrogel, the individual hydrogels can comprise the same polymer (or polymers), or different polymers.

In various embodiments, the hydrogel is crosslinked prior to application of the magnetic field, during application of the magnetic field or after application of the magnetic field.

In various embodiments, at least two magnetic fields are used to manipulate the magnetically labeled cells, either before, during or after crosslinking of the hydrogel. In yet other embodiments, three magnetic fields are used to manipulate the magnetically labeled cells, either before, during or after crosslinking of the hydrogel.

In yet another embodiment, a method for producing an organized engineered cell tissue is provided. The method comprises mixing a first plurality of magnetically labeled cells with a first cross-linkable hydrogel to form a first cell-hydrogel mixture, manipulating at least a portion of the first plurality of magnetically labeled cells with a magnetic field to arrange the magnetically labeled cells into a first specific cellular arrangement, crosslinking the first cross-linkable hydrogel, thereby forming a first organized engineered cell tissue; mixing a second plurality of magnetically labeled cells with a second cross-linkable hydrogel to form a second cell-hydrogel mixture, manipulating at least a portion of the second plurality of magnetically labeled cells with a magnetic field to arrange the magnetically labeled cells into a second specific cellular arrangement, crosslinking the second cross-linkable hydrogel, thereby forming a second organized engineered cell tissue; and combining the first and second organized engineered cell tissues.

BRIEF DESCRIPTION OF THE FIGURES

FIG. 16 (top-left) is a cartoon indicating the cell and particle orientation and alignment and the interface region of the fused hydrogels. FIG. 16 (bottom-right) is a higher magnification image of the interface of the fused hydrogels. FIG. 16 (bottom-left) is an image of the hydrogel with CSFE labeled cells, stained with Hoechst 33342, and shows columnar arrangements of magnetically labeled cells. The asterisk signifies the fusion interface.

FIG. 18 (right) are MRI images of defects filled with unlabeled or labeled chondrocytes.

FIG. 22 also shows images from an in situ transplantation of MagN97 labeled cells in New Zealand White Rabbit osteochondral defects. FIG. 22 (bottom-left) shows a defect in trochlear groove (3.2 mm×2 mm deep). FIG. 22 (bottom-middle) shows an image of iron oxide labeled cells being aligned via an external magnet (~500 gauss). FIG. 22 (bottom-right) shows the defect filled with iron oxide labeled cells in crosslinked alginate hydrogel.

Left: NArC particles have an approximated average size of 50 nm (distribution from ~10 to ~100 nm), with relatively tight and uniform particle size. Some particles are slightly faceted. Middle: MagN97 are, on average, 200 nm in diameter with a variation from ~70 to ~500 nm range. MagN97 are a mix of spherical to elongated shaped particles.

Right: MagN98 are on average around 30 nm in diameter (distribution mostly 10~40 nm), with relatively tight and uniform particle size. Some particles are slightly faceted.

DETAILED DESCRIPTION OF THE INVENTION

Definitions

A "magnetic particle", as used herein, can be either a nanoparticle or a microparticle. A plurality of magnetic particles, in one embodiment, includes particles with about the same diameter. In another embodiment, a plurality of magnetic particles comprises particles with different diameters. A magnetic particle, in one embodiment, is ferromagnetic or paramagnetic. In one embodiment, a plurality of magnetic particles comprises ferromagnetic and paramagnetic particles.

As used herein, a "magnetically-labeled cell" is a cell which has either taken up a magnetic particle, or a cell which is bound to a magnetic particle, for example, via an ionic or covalent bond.

A "hydrogel", as used herein, is comprised of one or more natural or synthetic polymers, or a combination thereof. The polymer(s) forms during one or more cross-linking/polymerization reactions. In one embodiment, heat or calcium chloride is used to crosslink a solution comprised of hydrogel monomers. A "hydrogel solution", as used herein, comprises uncrosslinked monomers, which are crosslinked/polymerized to form a hydrogel. In this regard, as used herein, "hydrogel solution" and "cross-linkable hydrogel" are used interchangeably.

Magnetic organoid patterning is a sophisticated example of employment of ferromagnetic particles in tissue engineering (Lin et al. (2008). Tissue Eng. Part C Methods 14, pp. 197-205). This technique involves labeling cells with RGD-conjugated magnetic particles to produce multicellular spheroids, which are manipulated via magnetic fields into distinct patterns for tissue production. However, this approach has drawbacks, as it may not be appropriate for all tissues where a three dimensional alignment at the level of single cells, rather than spheres, is more desirable or representative of the organ being reproduced.

The methods provided herein permit three dimension manipulations of cells with magnetic particles, and can be tailored to control the distance between cells, cell density, and cell orientation within a single hydrogel matrix, or multiple hydrogel matrices, without specialized "pre-functionalization" of magnetic particles. One embodiment of this method is provided in FIG. 1.

Figure 1:
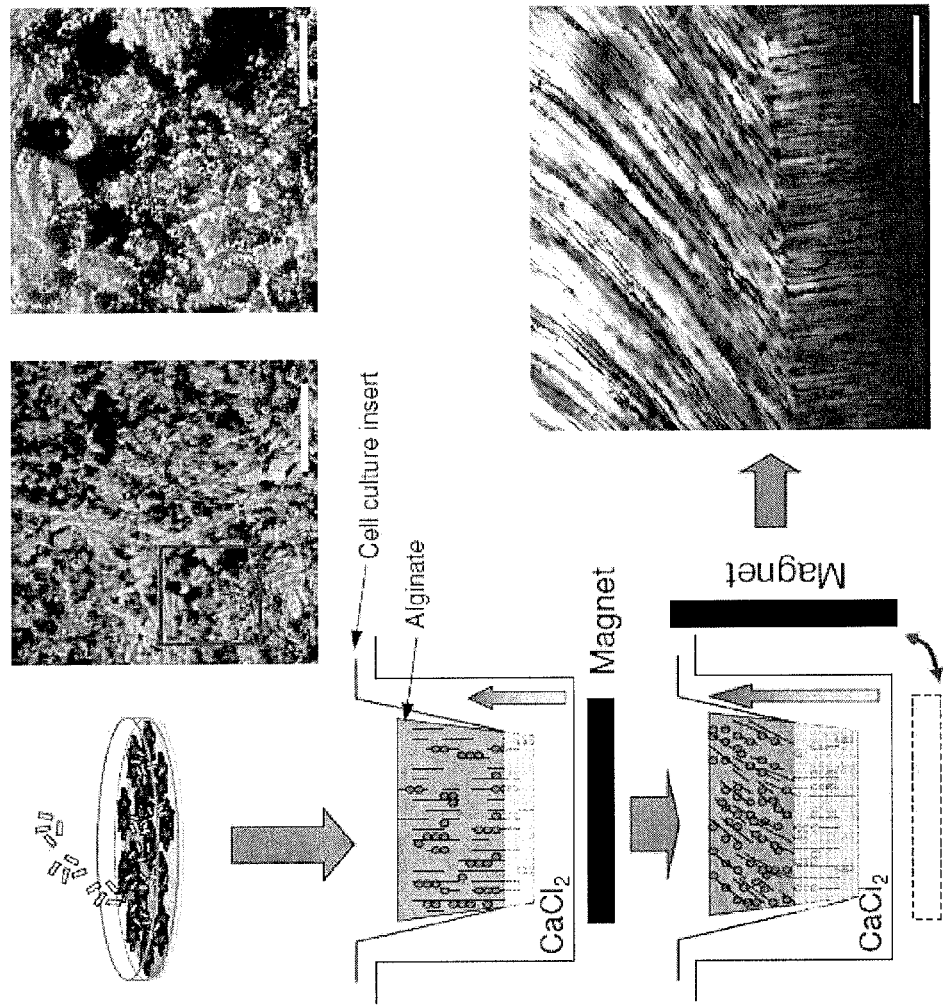
FIG. 1 is a flow chart showing one embodiment of the invention for producing multiple cell arrangements in a single hydrogel. A phase contrast image of chondrocyte monolayer culture with 5 mg/mL iron oxide MagN97 particles (scale bar 50 μm), and an inset of the image is also shown (scale bar 20 μm). Also shown is a micrograph of a cross linked alginate hydrogel containing iron-oxide labeled cells (scale bar 100 μm).

FIG. 1 shows one method for the production of multiple cell arrangements in a single alginate gel using ferromagnetic particles and magnetic fields. Magnetically-labeled cells, in this embodiment, are harvested from a cell culture and mixed with hydrogel solution, e.g., 2% alginate solution and transferred to a cell culture insert that is placed in a calcium chloride bath. In one embodiment, the cells/particles are aligned vertically using an external magnetic field. The direction of alginate crosslinking is denoted by the bold red arrow. As shown in FIG. 1, after a period of time (e.g., 2 minutes), the magnet is moved 90° to alter the alignment of the cells and bound particles. See also Example 4, below.

In one embodiment, prior to introducing magnetic particles, cells, e.g., chondrocytes, are grown in monolayer culture to a suitable confluence. In one embodiment, the cells are grown to at least 50% confluence, at least 60% confluence, at least 65% confluence, at least 70% confluence, at least 75% confluence, at least 80% confluence, at least 85% confluence, at least 90% confluence, or at least 95% confluence.

Cell types amenable for use in the present invention include, but are not limited to chondrocytes (cartilage), include chondroprogenitor cells, mesenchymal stem cells and other adult derived stem cells (e.g., from tissues listed in Table 1) and embryonic stem cells. In another embodiment, the cell type is based on the "tissue type" listed in Table 1, e.g., keratinocytes (skin); osteoblasts (bone); tenocytes (tendon); fibrocytes (ligament); endothelial; smooth muscle and fibroblast (blood vessel); cardiomyocyte (heart); skeletal myocyte (muscle); hepatocyte (liver); alpha; beta and delta cells (islets of Langerhans cells of the pancreas); enterocytes, paneth, enteroendocrine, goblet and tuft (intestine); glomerulus parietal; glomerulus podocyte, proximal tubule brush border cell, Loop of Henle thin segment cell, distal tubule cell and collecting duct cell (kidney); Ameloblast epithelial cell, cementocyte and odontocyte (teeth/dental); urinary epithelium cell (Ureter and Urethra); breast epithelium, cuboidal cells and myoepithelial cells (breast/mammary gland), and combinations thereof.

For example, in one embodiment, a monolayer culture is grown with at least two types of small intestine epithelium cells. In a further embodiment, the monolayer culture comprises at least two cell types selected from paneth cells, goblet cells, enterocytes and enteroendocrine cells.

Cell cultures can be seeded at various densities. For example, in one embodiment, cells, e.g., chondrocytes, are seeded in monolayer culture at a density of $10 \times 10^3$ cells per $cm^2$, $50 \times 10^3$ cells per $cm^2$, $10 \times 10^3$ cells per $cm^2$, $20 \times 10^3$ cells per $cm^2$, $30 \times 10^3$ cells per $cm^2$, $40 \times 10^3$ cells per $cm^2$, $50 \times 10^3$ cells per $cm^2$, $60 \times 10^3$ cells per $cm^2$, $70 \times 10^3$ cells per $cm^2$, $80 \times 10^3$ cells per $cm^2$, $90 \times 10^3$ cells per $cm^2$ or $10 \times 10^4$ cells per $cm^2$. Cell cultures are then grown to their desired confluence. For example, in one embodiment, cell cultures are grown for 12 hours, 18 hours or 24 hours, in order to reach the desired confluence.

Growth factors may also be added to the cells while in culture. For example, in one embodiment, for cartilage and bone cells, TGFβ1, TGFβ3, BMP2, BMP4, BMP6, BMP7, or a combination thereof, can be added during cell growth.

Once the cells reach their desired confluence, the cell culture medium, in one embodiment, is incubated with a plurality of magnetic particles, e.g., iron oxide particles, to magnetically label the cells. A cell is magnetically labeled by either uptake of one or more particles, or by binding one or more particles on the cell surface.

In an alternative embodiment, the cells are labeled in suspension with a plurality of magnetic particles, rather than in a monolayer culture. In a further embodiment, a chondrocyte cell suspension is labeled with a plurality of magnetic particles. In one embodiment, the plurality of magnetic particles has substantially the same diameter. In another embodiment, the plurality of magnetic particles include both paramagnetic and ferromagnetic particles.

In one embodiment, regardless of whether the cells are labeled in monolayer or in suspension, the cells are incubated with a concentration of magnetic particles of about 0.01 mg particle/mL cell culture medium (mg/mL), about 0.05 mg/mL, about 0.1 mg/mL, about 0.25 mg/mL, about 0.5 mg/mL, about 1 mg/mL, about 2 mg/mL, about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL or about 100 mg/mL, including all ranges and subranges thereof. In another embodiment, the cell culture is incubated with a concentration of magnetic particles that is at least about 0.01 mg/mL, at least about 0.05 mg/mL, at least about 0.1 mg/mL, at least about 0.25 mg/mL, at least about 0.5 mg/mL, at least about 1 mg/mL, at least about 2 mg/mL, at least about 5 mg/mL, at least about 10 mg/mL, at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL, including all ranges and subranges thereof.

The magnetic particles described herein are nanoparticles, microparticles or a combination thereof, and their respective positions can be manipulated upon the introduction of a magnetic field. The particles can be arranged in one or more specific patterns, in response to an external magnetic field. Therefore, once inside a cell, or bound to a cell's surface, the microparticles and nanoparticles are used to arrange cells in specific patterns within a hydrogel matrix.

Figure 24:
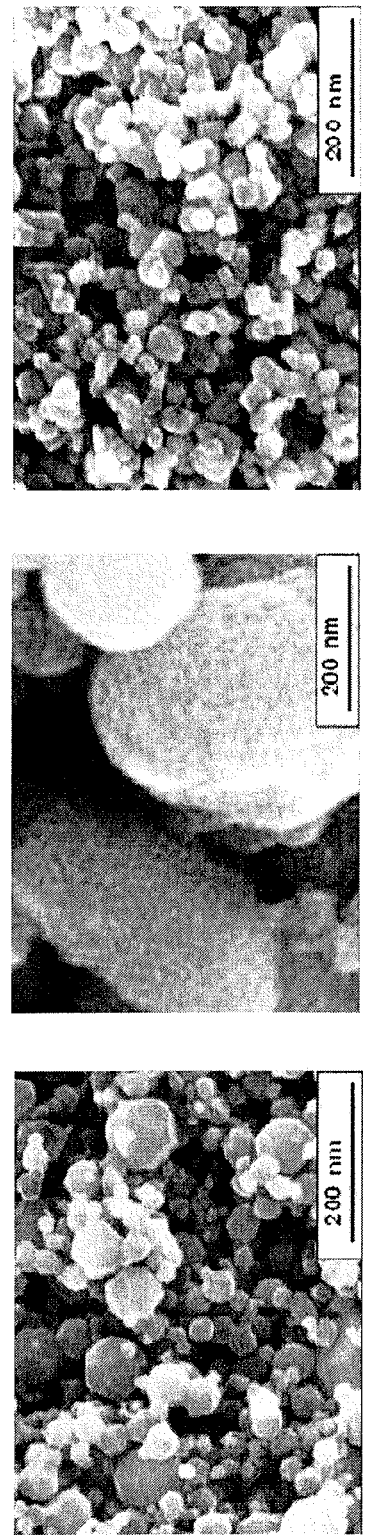
FIG. 24 are scanning electron micrographs of ferromagnetic iron oxide particles.

In one embodiment, the magnetic particles used in the methods of the invention are paramagnetic. In another embodiment, the magnetic particles are ferromagnetic (FIG. 24). In yet another embodiment, the magnet particles are both paramagnetic and ferromagnetic.

Soft-magnetic materials are amenable for use with the present invention. Iron-based magnets (e.g., Fe—Si, $Fe_{50}Co_{50}$, permalloy ($Ni_{90}Fe_{20}$)) have been used as soft-magnetic materials, and are one type of magnet that can be used with the present invention (Sellmyer and Skomski (2006). Appendix to *Advanced Magnetic Nanostructures*, Springer Science, pp. 491-496).

Iron oxide ferromagnetic particles have been used for non-invasive tracking and directing labeled cells in vivo (Arbab et al. (2004). Hum Gene Ther. 15, pp. 351-360; Henning et al. (2008). J Vis. Exp. 13, p. 685; Tallheden et al. (2006). Life Sci. 79, pp. 999-1006), for seeding labeled cells into scaffolds (Shimizu et al. (2006). J. Biomed. Mater. Res. B Appl. Biomater. 77, pp. 265-272); for bone tissue engineering (Shimizu et al. (2007). J. Biomed. Mater. Res. B Appl. Biomater. 82, pp. 471-480); for cell patterning or producing cell sheet layers consisting of various cell types, and to produce ring and tubular-like structures in urinary and vascular tissue engineering applications (Frasca et al. (2009). Langmuir 25, pp. 2348-2354; Ito et al. (2007). J. Biosci. Bioeng. 104, pp. 288-293; Lin et al. (2008). Tissue Eng. Part C Methods 14, pp. 197-205; Yamamoto et al. (2009). J. Biosci. Bioeng. 108, pp. 538-543).

In one embodiment, an iron oxide particle (or plurality thereof) selected from NanoArc Industrial maghemite ($Fe_2O_3$), 20-40 nm diameter, "NArc"; Magnetite ($Fe_3O_4$) 97%-325 mesh, ~44 µm diameter, "MagN97" and Magnetite ($Fe_3O_4$) 98% 20-30 nm diameter (MagN98) is used in the methods and the compositions of the present invention. Combinations of the three aforementioned particle types can also be employed. In another embodiment, $Fe_2O_3$ or $Fe_2O_4$ particles are employed, but the particles have a different diameter than the diameters provided above.

In another embodiment, a plurality of magnetic particles comprised of Co, Ni—Fe (permalloys), FePt, CoPt and Fe, or combinations thereof, is employed by the methods of the invention.

Other magnetic particles are also amenable for use with the invention. For example, in one embodiment, $CrO_2$ particles, or ferrite particles such as NiO-doped $Fe_2O_3$ or ZnO-doped $Fe_2O_3$ particles are employed. In another embodiment, metallic magnetic particles such as Co, Fe, CoPt, CoPd are used.

In one embodiment, the surfaces of the magnetic particles are coated and protected for corrosion resistance and biocompatibility. In a further embodiment, the coating comprises Au, Pt or Pd. In another embodiment, at least one surface of the majority of plurality of magnetic particles is coated and protected for corrosion resistance and biocompatibility. In a further embodiment, the coating comprises Au, Pt or Pd.

In one embodiment, the plurality of magnetic particles comprises magnetic particles that are spherical, oblong, elongated, or a combination thereof (see FIG. 24).

The plurality of magnetic particles, in one embodiment, have an average diameter selected from about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 200 nm, about 300 nm, about 400 nm, about 500 nm, about 600 nm, about 700 nm, about 800 nm, about 900 nm, or about 1 µm, including combinations of diameters, and all ranges and subranges thereof.

In another embodiment, the plurality of magnetic particles have an average diameter selected from about 1.5 µm, about 2 µm, about 3 µm, about 4 µm, about 5 µm, about 6 µm, about 7 µm, about 8 µm, about 9 µm, about 10 µm, about 20 µm, about 30 µm, about 40 µm, about 50 µm, about 60 µm, about 70 µm, about 80 µm, about 90 µm or about 100 µm, including combinations of diameters, and all ranges and subranges thereof.

A cell culture, in one embodiment, is incubated with the plurality of magnetic particles for a time sufficient to allow for cells in the culture or cell suspension to bind, or uptake, the magnetic particles. The magnetic particles, after binding to the cells or uptake by the cells, in one embodiment remain in the cell culture medium or cell suspension to ensure optimal uptake and/or binding.

In one embodiment, the cell culture or cell suspension is incubated with the magnetic particles for at least about 10 seconds, at least about 20 seconds, at least about 30 seconds, at least about 1 min., at least about 2 min., at least about 3 min., at least about 4 min. at least about 5 min., at least about 10 min., at least about 15 min., at least about 20 min., at least about 25 min., at least about 30 min., at least about 35 min., at least about 40 min., at least about 45 min., at least about 50 min., at least about 55 min., at least about 1 hr., at least about 2 hr., at least about 3 hr., at least about 4 hr., at least about 5 hr., at least about 6 hr., at least about 7 hr., at least about 8 hr., at least about 10 hr., at least about 12 hr., at least about 14 hr., at least about 16 hr., at least about 18 hr., at least about 20 hr., at least about 22 hr., at least about 24 hr., at least about 36 hr., at least about 48 hr., at least about 60 hr., at least about 72 hr., at least about 1 week or at least about 2 weeks. In a further embodiment, the concentration of magnetic particle is selected from a concentration given herein.

In another embodiment, the cell culture is incubated with the plurality of magnetic particles for about 10 seconds, about 20 seconds, about 30 seconds, about 1 min. about 2 min., about 3 min., about 4 min., about 5 min., about 10 min., about 15 min., about 30 min., about 35 min., about 40 min., about 45 min., about 50 min., about 55 min., 1 hr., about 2 hr., about 3 hr., about 4 hr., about 5 hr., about 6 hr., about 7 hr., about 8 hr., about 10 hr., about 12 hr., about 14 hr., about 16 hr., about 18 hr., about 20 hr., about 22 hr., about 24 hr., about 36 hr., about 48 hr., about 60 hr. or about 72 hr., including ranges and subranges thereof. In a further embodiment, the concentration of magnetic particle is selected from a concentration given above.

In one embodiment, once the cells in culture bind or take up the particles, the cell culture medium (e.g., DMEM) is removed and the cells are washed in order to remove any unbound particles. For example, in one embodiment, the cell culture medium is aspirated after magnetic particle uptake/binding. In a further embodiment, the cells in culture are washed with 1×PBS after the medium is aspirated. Cell cultures can be washed multiple times, if desired. In one embodiment, the cells in culture are washed at least once, at least 2× or at least 3× after interaction with the plurality of magnetic particles.

In one embodiment, chondrocytes are seeded in monolayer culture at a density of $50 \times 10^3$ cells per $cm^2$ and cultured for 24 hours, or about 24 hours. Magnetic particles (e.g., 1 mg/mL) are added to the cell culture medium and incubated for about 2 hours prior to washing cells to remove unbound particles.

In another embodiment, unbound particles are not removed. This may be desirable in order to add more strength/mechanical stability to the hydrogel. In another embodiment, magnetic particles derivatized with growth factors are present in the cell culture with the magnetically labeled cells, to promote tissue growth.

The magnetically labeled cells are harvested and mixed with a solution of uncrosslinked hydrogel. For example, in one embodiment, the cells are harvested by washing in 1×PBS, and then detached from the culture plate, e.g., by using either trypsin or accutase. The cells form a suspension in the reagent used for detachment. The cell suspension, in one embodiment, is further diluted, e.g., with 1×PBS.

In one embodiment, cells are detached during the 1×PBS wash by using a rubber policeman. A cell suspension in 1×PBS is therefore formed in this embodiment. In another embodiment, cells are detached by adding a hydrogel solution directly to the cell culture dish/well/plate. In this embodiment, cell culture medium is first aspirated. In a further embodiment, a rubber policeman is used to assist in the detachment of cells from the culture dish/well/plate.

The cell suspension, in one embodiment, is then mixed with a hydrogel solution (i.e., a solution of non-crosslinked hydrogel). In a further embodiment, the cell suspension is mixed with 2% alginate.

In one embodiment, the cell suspension is mixed in an about 1:1 volume ratio with the uncrosslinked hydrogel solution (e.g., 2% alginate). In another embodiment, the cell suspension is mixed in an about 1:2 v/v ratio with the hydrogel solution, an about 1:3 v/v ratio with the hydrogel solution, an about 1:4 v/v ratio with the hydrogel solution, an about 1:4 v/v ratio with the hydrogel solution, an about 1:5 v/v ratio with the hydrogel solution, an about 1:6 v/v ratio with the hydrogel solution, an about 1:7 v/v ratio with the hydrogel solution, an about 1:8 v/v ratio with the hydrogel solution, an about 1:9 v/v ratio with the hydrogel solution, an about 1:10 v/v ratio with the hydrogel solution, an about 2:1 v/v ratio with the hydrogel solution, an about 3:1 v/v ratio with the hydrogel solution, an about 4:1 v/v ratio with the hydrogel solution, an about 5:1 v/v ratio with the hydrogel solution, an about 6:1 v/v ratio with the hydrogel solution, an about 7:1 v/v ratio with the hydrogel solution, an about 8:1 v/v ratio with the hydrogel solution, an about 9:1 v/v ratio with the hydrogel solution or an about 10:1 v/v ratio with the hydrogel solution.

In one embodiment, the cells in the harvested cell suspension are counted prior to mixing the cell suspension with the uncrosslinked hydrogel. In this manner, a defined number of cells can be mixed with the hydrogel solution. In one embodiment, about $1 \times 10^4$ cells, about $2 \times 10^4$ cells, about $3 \times 10^4$ cells, about $4 \times 10^4$ cells, about $5 \times 10^4$ cells, about $6 \times 10^4$ cells, about $7 \times 10^4$ cells, about $8 \times 10^4$ cells, about $9 \times 10^4$ cells, about $1 \times 10^5$ cells, about $2 \times 10^5$ cells, about $3 \times 10^5$ cells, about $4 \times 10^5$ cells, about $5 \times 10^5$ cells, about $6 \times 10^5$ cells, about $7 \times 10^5$ cells, about $8 \times 10^5$ cells, about $9 \times 10^5$ cells, $1 \times 10^6$ cells, about $2 \times 10^6$ cells, about $3 \times 10^6$ cells, about $4 \times 10^6$ cells, about $5 \times 10^6$ cells, about $6 \times 10^6$ cells, about $7 \times 10^6$ cells, about $8 \times 10^6$ cells, about $9 \times 10^6$ cells, about $10 \times 10^6$ cells, about $20 \times 10^6$ cells, about $30 \times 10^6$ cells, about $40 \times 10^6$ cells, about $50 \times 10^6$ cells, or about $60 \times 10^6$ cells, are mixed with the uncrosslinked hydrogel. In a further embodiment, the cells are mixed in one of the v/v ratios given herein.

Hydrogels for Use with the Invention

As described above, the present invention, in one embodiment, is directed to a biocompatible hydrogel as a tissue engineering scaffold. The scaffold provides a mechanical support and environment to enhance cell migration and growth. Therefore, the use of a tissue engineering scaffold, in one embodiment, accelerates the regeneration of tissue.

The hydrogel scaffold is polymer based, and when crosslinked, forms a permeable membrane. Therefore, in its uncrosslinked form, a hydrogel exists as a solution and includes the monomer subunits which eventually polymerize.

Because the membrane is permeable, it allows the exchange of nutrients, oxygen and biotherapeutic substances between the cells in the hydrogel matrix and the surroundings.

In one embodiment, the hydrogel scaffold acts as a barrier and occludes the entrance of undesirable cell types into the scaffold area. For example, the scaffold, in one embodiment, prevents the entrance of high molecular weight immunoresponsive agents into the scaffold, and therefore, the implant site.

The present invention is not limited to one particular type of hydrogel. Both natural and synthetic polymers can be employed as hydrogel scaffolds, so long as the polymers are biocompatible and exhibit certain desirable characteristics. For example, it is desirable for the hydrogel to exhibit one or more of the following properties (1) the promotion of cell growth;
(2) the hydrogel, when cross-linked, should not damage the cells;
(3) allow for the diffusion of nutrients and metabolites between the cells in the hydrogel scaffold and the scaffold's surroundings;
(4) the ability to degrade into noncytotoxic components n response to the production of extracellular matrix ("ECM") components.

Other advantages and properties of hydrogels for use with the present invention are provided by Varghese and Elisseeff (2006). Adv. Polym. Sci. 203, pp. 95-144, the contents of which are incorporated by reference in their entirety for all purposes. Additionally, hydrogels can be selected based on mechanical properties, in order to match the type of tissue being repaired or generated.

Natural Hydrogels

Natural hydrogels are desirable for their ability to mimic aspects of the native ECM, thereby facilitating cell adherence, cell migration, cell division and differentiation and ECM deposition (Nöth et al. (2010). Advanced Drug Delivery Reviews 62, pp. 765-783).

Non-limiting examples of natural hydrogels for use with the present invention include collagen, gelatin, hyaluronan (also referred to as "hyaluronic acid", "hyaluronate" or "HA"), fibrin, chondroitin sulfate ("CS"), a gelatinous protein mixture secreted by Engelbreth-Hohn-Swarm (EHS) mouse sarcoma cells (sold under the tradename Matrigel™), alginate, chitosan, fibrin, agarose, silk, and combinations thereof. As described above, a hydrogel solution comprises hydrogel monomers which eventually form the hydrogel matrix during a crosslinking/polymerization reaction. One of ordinary skill in the art will understand that the hydrogel solution may comprise hydrogel polymers, e.g., if polymerization can take place at room temperature.

Alginate

Alginate, an anionic polysaccharide polymer found in seaweed, is formed from β-D-mannuronic acid and L-guluronic acid. Alignate forms a gel under physiological conditions, in the presence of alkaline earth metals, for example divalent ions such as $Ca^{2+}$, $Ba^{2+}$ and $Sr^{2+}$, through ionic interaction between the carboxylic group located on the polymer backbone and the particular cation.

In one embodiment, in order to control the molecular weight of alginate polymer chains when degraded in situ, and therefore, in order to generate bioresorbable dissolution products, the alginate solution is treated with γ-irradiation prior to gelation (Hong et al. (2004). Adv Mater 16, p. 1917). Alginate polymer chains can also be partially oxidized to render the chains hydrolytically degradable (Bouhadir et al. (2001). Biotech. Prog. 17, p. 945).

Alginate polymers have been found to support bone formation, as well as to promote cell growth and deposition of ECM for chondrocytes and adult mesenchymal stem cells ("MSCs") in vitro and in vivo (Alsberg et al. (2003). J. Dent. Res. 82, p. 903; Gaissmaier et al. (2005). Biomaterials 26, pp. 1953-1960; Akeda et al. (2006). Osteoarthritis Cartilage 14, pp. 1272-1280; Steinert et al. (2003). J. Orthop. Res. 21, pp. 1090-1097; Simmons et al. (2004). Bone 35, pp. 562-569).

In one embodiment, a 2% alginate solution is used as the hydrogel solution. In a further embodiment, an alginate solution is mixed with a cell suspension and the final concentration of alginate in the cell-alginate mixture is 2% w/w or 2% w/v.

Collagen

Because collagen is the major structural component of the ECM, and connective tissues such as tendon, meniscus, vertebral disc constructs, ligament, cartilage, bone and skin, it can be used as a hydrogel scaffolding material for tissue regeneration. Collagen type I, type II, or a combination thereof may be employed as a hydrogel in the methods described herein.

Collagen is composed of three polypeptide chains, each forming the structure of a left-handed helix. The three helices are wrapped around each other, and form a triple-helix, and the helix is stabilized by hydrogen bonds. A thermally reversible collagen hydrogel is formed when the collagen triple helix entangles with other helices via secondary interactions. In one embodiment, the mechanical properties of the collagen hydrogel are increased by introducing various chemical crosslinks.

Collagen hydrogels have been used to synthesize artificial skin, and as scaffolds for engineering liver, skin, bone, cartilage and blood vessels (Varghese and Elisseeff (2006). Adv. Polym. Sci. 203, pp. 95-144).

Gelatin

When collagen is denatured by alkaline or acid treatment, the polyelectrolyte gelatin is formed. Gelatin hydrogels are formed, in one embodiment, by chemical crosslinking with bifunctional agents such as glutaraldehyde and water-soluble carbodiimide (Young et al. (2005). J. Control. Release 109, pp. 256-274). Bone, cartilage, skin and fat tissue regeneration applications have employed gelatin (Nöth et al. (2010). Advanced Drug Delivery Reviews 62, pp. 765-783).

Fibrin

Under physiological conditions, fibrin is a fibrous strand, and is produced during blood clot formation by the enzymatic action of thrombin on glycoprotein fibrinogen. Similarly, a fibrin hydrogel is formed the enzymatic polymerization of fibrinogen by thrombin. Fibrin-based materials, including fibrogen hydrogels, have been used to engineer various tissues such as cartilage, bone, cardiovascular, and chronic wound healing and bone grafts (Varghese and Elisseeff (2006). Adv. Polym. Sci. 203, pp. 95-144).

Hyaluronan (Hyaluronic Acid or HA)

HA is found in all mammalian tissues (e.g., connective tissue) and body fluids, and the excellent lubrication property of mammalian joints is mainly attributed to the presence of HA within the joints. HA is a non-sulfated glycosaminoglycan, and is composed of N-acetyl-D-glucosamine and D-glucuronic acid subunits.

HA has been reported to be associated with ECM fluid regulation, structural integrity of tissue and viscoelastic properties of tissue (Nöth et al. (2010). Advanced Drug Delivery Reviews 62, pp. 765-783). It has also been reported to be prevalent during wound healing, and to play a role in embryonic development, morphogenesis and angiogenesis (Chen and Abatangelo (1999). Wound Rep. Reg. 7, p. 79-89).

Chitosan

The cationic polymer chitosan, derived from chitin, is a linear polysaccharide composed of D-glucosamine and N-acetyl-D-glucosamine residues. Chitosan has been reported to be renewable, biodegradable (e.g., chitosan can be enzymatically degraded in vivo by lysozyme and chytosanasitase), biocompatible, non-toxic and non-antigenic, and therefore, shows promise for use as a hydrogel for tissue engineering applications (Khor and Lim (2003). Biomaterials 24, pp. 2239-2349; Di Martino et al. (2005). Biomaterials 26, pp. 5983-5990). Specifically, chitosan hydrogels have been used to investigate bone regeneration and chondrogenesis (Lahiji et al. (2000). J. Biomed. Mater. Res. 51, p. 586; Muzzarelli et al. (1994). Biomaterials 15, p. 1075).

Other advantages of chitosan include its structurally similarity to GAG, and its ability to undergo thermal and pH induced gelation.

Matrigel™

The Matrigel™ matrix is available from BD Biosciences, and is a gelatinous protein mixture extracted from mouse sarcoma cells. Matrigel™ is comprised of laminin, collagen IV, heparan sulfate proteoglycans and entactin. Matrigel™ polymerizes at room temperature to form a hydrogel which resembles the basement membrane of mammalian cells.

Silk

Silk hydrogels are mechanically robust, e.g., silk has a modulus and tensile strength comparable to strong man-made fibers such as Kevlar® (Kitagawa and Kitayama (1997). J. Mater. Sci. 32, p. 2005). The mechanical properties of silk have allowed the material to be used to make scaffolds to engineer ligaments, bone and cartilage. Additionally, silk has been reported to degrade completely within two years in vivo (Vunjak-Novakovic et al. (2004). Annu. Rev. Biomed. Eng. 6, p. 131).

Chondroitin Sulfate (CS)

The disaccharide chondroitin sulfate is composed of glucuronic acid and N-acetylgalactosamine, and occupies approximately 80% of glycosaminoglycan (GAG), a component of articular cartilage. CS is implicated in the modulation of growth factor and cytokine binding, and the regulation of cell adhesion, migration, proliferation and differentiation.

CS based hydrogels have been reported to achieve enhanced cell proliferation and proteoglycan secretion (Bryant et al. (2004). Macromolecules 37, p. 6726; Li et al. (2004). J. Biomed. Mater. Res. 68A, p. 28; Pieper et al. (1999). Biomaterials 20, p. 847).

Synthetic Hydrogels

A synthetic hydrogel may be desirable for its ability, in some instances, to provide more structural stability, and/or its ability to more readily form the shape and structure of the targeted tissue or organ. Additionally, because the hydrogel is synthetic, properties such as degradation profile, mechanical and structural properties, and hydrophilic-hydrophobic balance may be individually tailored.

In one embodiment, the hydrogel used in the present invention is a synthetic biodegradable polymer. In another embodiment, the synthetic biodegradable polymer is selected from an FDA-approved polyester. In yet another embodiment, the synthetic polymer, for use with the present invention as a hydrogel, is selected from poly(lactic acid) ("PLA"), poly(glycolic acid) ("PGA"), the copolymer poly(lactic-glycolic) acid ("PLGA"), polymers and copolymers of ethylene oxide, poly(ethylene oxide), poly(ethylene glycol diacrylate), polymers and copolymers of vinyl alcohol, poly(vinyl alcohol), polymers and copolymers of acrylic or methacrylic acid, poly(acrylic acid), poly(acrylamidomethyl propane sulfonic acid), poly(hydroxylethyl methacrylate), poly(propylene fumarate-co-ethylene glycol), and combinations thereof.

Transfer to Tissue Defect In Situ or Growth of Neotissue In Vitro

Once the magnetically labeled cells are mixed with the hydrogel solution at a given ratio, the mixture, in one embodiment, is transferred to a cell culture insert or a tissue defect in situ.

As used herein, a "tissue defect" refers to a flaw or space in a tissue, as compared to the healthy tissue. For example, the methods presented herein, in one embodiment, are used to regenerate tissue in a soft tissue defect or a bone defect (for example a subchondral defect). Examples of soft tissue defects include defects in tendon, ligament, fascia, skin, fibrous tissue, connective tissue, muscles, nerves and blood vessels.

The present invention is not limited to replacement of a particular type of tissue or organ. In one embodiment, the invention regenerates tissue or organ(s) that are missing or damaged because of disease, injury or surgical removal. Additionally, the invention is not limited to the treatment of the particular tissue defects and/or tissue degeneration disclosed herein.

The methods provided herein are amenable for use in an array of tissue engineering applications. For example, in one embodiment, the methods are used to correct tissue defects, to treat tissue degeneration, or to replace tissue or organs (e.g., tissue or organ(s) are missing or damage because of disease, injury or surgical removal)

Table 1 provides a non-limiting list of tissue types that can be engineered by the methods of the present invention. Table 1 also provides specific indications where tissue engineering may be useful, and where tissue defects may arise. The number of patients/procedures per year for each of these indications is described in Varghese and Elisseeff (2006). Adv. Polym. Sci. 203, pp. 95-144.

TABLE 1

Tissue types that can be engineered by the methods of the present invention.

| Tissue/Cell type | Indication/defect for engineered cells/tissue |
|---|---|
| Skin | Burns, pressure sores, venous stasis ulcers, diabetic ulcers |
| Bone | Joint replacement, bone graft, internal fixation, facial reconstruction |
| Cartilage | Patella resurfacing, chondomalacia patellae, meniscal repair, arthritis (e.g., knee or hip arthritis), finger and small joint replacement, osteochondritis dissecans |
| Tendon | Tendon repair |
| Ligament | Ligament repair |
| Blood vessels | Heart vessel repair, large vessel repair, small vessel repair |
| Liver | Metabolic disorders, liver cirrhosis, liver cancer |
| Pancreas | Repair, regeneration, or replacement |
| Intestine | Repair, regeneration, or replacement |
| Kidney | Repair, regeneration, or replacement |
| Dental | Tooth repair, regeneration or replacement |
| Bladder | Repair, regeneration, or replacement |
| Ureter | Repair, regeneration, or replacement |
| Urethra | Repair, regeneration, or replacement |
| Breast | Repair, regeneration, or replacement |

As described above, a magnetically labeled cell:hydrogel mixture is used, in one embodiment, to repair tissue defects, or to grow neotissue in vitro. Additionally, as described above, the magnetically labeled cell:hydrogel mixture is either transferred to a cell culture insert or a tissue defect, prior to crosslinking the hydrogel. It should be noted that the hydrogel, in one embodiment, may crosslink at room temperature. Therefore, some crosslinking may take place prior to transfer to the cell culture insert or tissue defect.

The specific cellular arrangement, in one embodiment, is manipulated by one or more magnetic fields prior to crosslinking the hydrogel. Alternatively or additionally, the cellular arrangement is manipulated by one or more magnetic fields during the crosslinking process. The one or more magnetic fields, in one embodiment, are applied simultaneously to the magnetically labeled cell:hydrogel mixture. Alternatively or additionally, one more magnetic fields are applied serially to the magnetically labeled cell:hydrogel mixture. In one embodiment, three magnetic fields are applied to the magnetically labeled cell:hydrogel mixture before, during or after the crosslinking process.

In one embodiment, the magnetically labeled cells are manipulated by one or more magnetic fields after crosslinking the hydrogel solution. In another embodiment, the magnetically labeled cells are manipulated after crosslinking by exerting force on the tissue.

In one embodiment, one magnetic field (generated by an external magnet) is used to align the magnetically labeled cells vertically in the tissue defect or in the cell culture insert, prior to, or during crosslinking of the hydrogel. In a further embodiment, the alignment of the cells is altered by changing the orientation of the magnetic field, for example by 45° or 90°, in relation to the original magnetic field.

In one embodiment, the magnetic field orientation is changed about 30 seconds after the first magnetic field is applied, about 45 seconds after the first magnetic field is applied, about 60 seconds after the first magnetic field is applied, about 75 seconds after the first magnetic field is applied, about 90 seconds after the first magnetic field is applied, about 2 minutes after the first magnetic field is applied, about 3 minutes after the first magnetic field is applied, about 4 minutes after the first magnetic field is applied, or about 5 minutes after the first magnetic field is applied.

In one embodiment, multiple magnetic fields are applied simultaneously to the hydrogel-cell mixture (e.g., 2, 3, 4 or 5 magnetic fields). As described above, in one embodiment, the magnetic field(s) is applied before or during crosslinking of the hydrogel, or both before and during crosslinking. In one embodiment, two magnetic fields are applied simultaneously, and the magnets which generate the magnetic field are oriented perpendicular to one another. In another embodiment, the magnets are oriented parallel to one another.

In another embodiment, at least three or at least four magnetic fields are applied to the magnetically labeled cell:hydrogel mixture, simultaneously, serially, or a combination thereof. In a further embodiment, at least three or at least four magnetic field(s) are applied before crosslinking, during crosslinking or before and during hydrogel crosslinking. In another embodiment, cells are manipulated via one or magnetic fields after the hydrogel has been crosslinked.

The magnetic fields for use with the invention are of a sufficient strength, and are applied for a sufficient time, to manipulate the magnetically labeled cells' orientations within the hydrogel matrix (before and/or during crosslinking). For example, in one embodiment, the strength of the one or more magnetic fields is about 25 gauss (G), about 50 G, about 75 G, about 100 G, about 150 G, about 200 G, about 250 G, about 300 G, about 350 G, about 400 G, about 450 G, about 500 G, about 550 G, about 600 G, about 650 G, about 700 G, about 750 G, about 800 G, about 850 G, about 900 G, about 950 G, about 1000 G, about 1500 G, or about 2000 G.

The magnetic field, in one embodiment, is tailored depending on the type and concentration of magnetic particle employed and the hydrogel composition. If multiple magnetic fields are applied simultaneously, the magnetic field strengths can be the same or different. Similarly, if magnetic fields are applied serially to the hydrogel-cell mixture, the strength of these fields can be the same or different.

As described above, the hydrogel is crosslinked after, during, or after and during cellular alignment with one or more magnetic fields. The crosslinking method is dependent upon the hydrogel employed in the invention. In one embodiment, crosslinking of the hydrogel solution occurs through ionic or covalent bonds, or a combination thereof. For example, divalent cations are used in one embodiment in order to crosslink an alginate hydrogel.

In one embodiment, crosslinking occurs at room temperature.

Other crosslinking methods include, but are not limited to, heat, radiation (e.g., γ-radiation), UV light, visible light, anions, cations, crystallization, hydrophilic-hydrophobic interactions, hydrogen bonding, molecular recognition and self assembly.

The present invention is not limited to particular crosslinking methods, or types of crosslinking reagents. Rather, certain agents/methods are useful, depending on the type of hydrogel employed. For example, an alginate hydrogel, in one embodiment, is crosslinked with calcium chloride, PEG/UV or light via photo-initiator. A hyaluronic acid (HA) or HA-tyramine based hydrogel, in one embodiment, is crosslinked with $H_2O_2$ or horseradish peroxidase (Lee et al. (2008). Softmatter. 4, pp. 880-887). A collagen hydrogel, in one embodiment, is crosslinked via a temperature change (e.g., liquid at 4° C. and solid gel at 37° C.). In another embodiment, an agarose hydrogel is crosslinked via a temperature change (melting at 65° C., still fluid at 40° C. for cell inclusion, and solidified gels (i.e., crosslinked) at 28° C.).

In one embodiment, a crosslinking gradient is employed in order to vary the crosslinking in the hydrogel. For example, in one embodiment, a cation gradient, e.g., $Ca^{2+}$ gradient, is used in order to vary the crosslinking in a single hydrogel, for example an alginate hydrogel. A crosslinking gradient, in one embodiment, is accomplished by applying different amounts of heat, UV light or radiation (e.g., γ-radiation) to specific portions of the hydrogel.

Multi-Layered Hydrogels

In one embodiment, two or more hydrogels are the same or different, and are fused together to form multilayer hydrogels. The individual hydrogels can each be comprised of the same hydrogel material, or can each be composed of a different hydrogel material (e.g., collagen and alginate). In one embodiment, HA and collagen type II are combined to form a multi-layer hydrogel (e.g., by the method disclosed by Taguchi et al. (2002). J. Biomater. Sci Polym. Ed. 13, pp. 43-52). In another embodiment, a multilayer structure is formed from chitosan, nano-hydroxyapatite and collagen, for example by the method disclosed by Huanga et al. (Huanga et al., (2011). Materials Science and Engineering: C. 31, pp. 683-687).

Fusing hydrogels together may be beneficial. In one embodiment, the formation of multiple arrangements in a single hydrogel structure (e.g., a multi-layer hydrogel) can, in one embodiment, generate a "hinge" effect, which is a result of the particles aligning and forming strands that are not easily disrupted, even following a change in the magnetic field orientation. In one embodiment, the "hinge" effect is accomplished by fusing multiple hydrogels together, or by varying the crosslinking degree in a single hydrogel matrix.

In one embodiment, the present invention is directed to methods for forming multilayer hydrogels. The layering of hydrogels provides the ability to generate more complex three dimensional tissue architecture, and allows for a more precise mimicking of the tissue to be repaired or generated. In one embodiment, a multilayer hydrogel is provided, and each layer of the hydrogel has a unique cellular arrangement. In one embodiment, the hydrogels in each layer are the same (e.g., both hydrogels are comprised of alginate). In another embodiment, the hydrogel composition of one layer differs from the hydrogel in at least a second hydrogel layer.

In another embodiment, a two layer hydrogel, or a three layer hydrogel, or a four layer hydrogel, or a five layer hydrogel is provided. The layers of the hydrogel can have the same or different cellular alignments and/or the same or different cell densities.

In one embodiment, two prealigned and crosslinked hydrogels are fused together to form a multi-layer hydrogel. For the purpose of this embodiment, hydrogels amenable to cation crosslinking are described. However, other hydrogels can be fused together.

To fuse both gels, in one embodiment, the surface of one hydrogel is exposed to a sodium citrate solution, in one embodiment, to partly dissolve the hydrogel surface (e.g., an alginate hydrogel surface) for about 30 seconds, about 1 minute, about 90 seconds, about 2 minutes, about 2 minutes 30 seconds, about 3 minutes, about 4 minutes or about 5 minutes, including ranges and subranges thereof. For example, filter paper, in one embodiment is soaked in a sodium citrate solution and placed on one surface of a crosslinked hydrogel, e.g., a cross-linked alginate hydrogel.

The second hydrogel, in one embodiment, is an alginate hydrogel, and is placed on the first hydrogel's soaked surface for a further period of time (e.g., about 1 min., about 2 min., about 3 min., about 4 min. about 5 min., about 6 min., about 7 min., about 8 min., about 9 min. or about 10 min., including ranges and subranges thereof) before the gels are fused. Next, the gels are fused by exposing the layered gels to $CaCl_2$.

The hydrogels can be fused by other methods. For example, agarose gels, in one embodiment, are fused together by changing the temperature of the gels. In one embodiment, UV light is used to fuse polyethylene glycol gels. Chemical crosslinking of two gels can also be employed, for example, collagen gels, in one embodiment, are fused together with lysyl hydroxylase.

EXAMPLES

The present invention is further illustrated by reference to the following Examples. However, it should be noted that these Examples, like the embodiments described above, are illustrative and are not to be construed as restricting the scope of the invention in any way.

Unless otherwise indicated, the materials used in the following examples were prepared according to the following methods and procedures.

Cartilage Procurement and Chondrocyte Isolation

Human articular cartilage was obtained from tissue banks (approved by Scripps institutional review board). Chondrocytes were isolated from full-thickness cartilage shavings via enzymatic digestion and cultured in monolayer for one passage in DMEM (Mediatech Inc, Manassas, Va.) supplemented with 10% calf serum (Omega Scientific Inc., Tarzana, Calif.) and Penicillin/Streptomycin/Gentomycin (Invitrogen, Carlsbad, Calif.) as previously detailed (Grogan et al. (2009). Arthritis Res. Ther. 11, p. R85).

Magnets

Barium ferrite magnets (1×4×6 inch; 900 gauss) and N45, Ni—CU—Ni coated rare earth neodymium disc magnets (10 lbs pulling force; 100-500 gauss) were used to arrange particles and cells in hydrogel.

Cell Staining

Live/dead staining (calcein-AM and ethidium homodimer-1) was performed as reported by Grogan et al. using confocal microscopy (LSM 510, Zeiss, Hamburg, Germany) (Grogan et al. (2003). J. Pathol. 198, pp. 5-13).

The number of live cells was assessed using an image analysis script written in MATLAB (MathWorks, Natick, Mass.). Viability is reported as percentage of live cells.

Pellet Cultures

A number of human chondrocyte pellets cultures ($5 \times 10^5$ cells each) were formed in the presence of one species of iron oxide particle (1 mg/mL). Three types of iron oxide particles were tested:

(i) NanoArc Industrial maghemite ($Fe_2O_3$), 20-40 nm diameter, "NArc";
(ii) Magnetite ($Fe_3O_4$) 97%-325 mesh, ~44 μm diameter, "MagN97" and
(iii) Magnetite ($Fe_3O_4$) 98% 20-30 nm diameter (MagN98).

Each pellet was cultured in serum-free ITS+ medium supplemented with TGFβ1 (10 ng/mL) as described by Barbero et al. for 12 days (Barbero et al. (2004). Osteoarthritis Cartilage 12, pp. 476-484). The medium was changed every 3 days. After 12 days, some pellets were fixed and embedded in paraffin for histology, while other pellets were prepared for RNA extraction for gene expression analysis.

Histology and Neocartilage Grading (Bern Score)

12-day old pellets were fixed in Z-Fix (ANATECH, Battle Creek, Mich.) and paraffin embedded. Sections of 4-5 μm were made for Safranin O-fast green staining. Immunohistochemical (IHC) analyses of collagen type II was performed using conditions previously described (Grogan et al. (2009). Arthritis Res. Ther. 11, p. R85). Neocartilage quality was assessed (two observers) using the Bern Score (Grogan et al. (2006). Tissue Eng. 12, pp. 2141-2149), which quantifies the intensity of Safranin O stain, distance between cells or the amount of extracellular matrix produced, and cell morphology.

Carboxyfluorescein Succinimidyl Ester (CSFE) Staining

CFSE is a fluorescent dye that was used to measure cell proliferation in flow cytometry assays. CFSE is transported into the cell during incubation with mononuclear cells binding covalently to cytoplasmic proteins, without adversely affecting cellular function. Analysis of cell division is determined through measuring CSFE intensity by flow cytometry. With each cell division, the fluorescent intensity per cell division is reduced 50%, thus providing a readout of the mitotic activity within a specific population of cells.

Human chondrocytes cultured in T75 $cm^2$ flasks were expanded to 70-80% confluence in DMEM with 10% calf serum. A stock solution of 5 mM CFSE (Invitrogen, Carlsbad, Calif.) was diluted in 10 mL PBS to a final concentration of 5 μM and pre-warmed to 37° C. Prior to applying the CSFE, the medium was removed and the cells were washed with 1×PBS once. the pre-warmed CSFE/PBS solution was added to the cells. The cells were incubated with the pre-warmed CSFE/PBS solution for 15 min. at 37° C. The CSFE solution was removed via aspiration and washed twice with 1×PBS before adding fresh medium to the cells.

Arrangement of Iron oxide Particles in Agarose

A plurality of each particle type was suspended at 5 mg/mL in 1% agarose (Ultra Pure, Invitrogen, Carlsbad, Calif.) in the presence or absence of a magnetic field (approximately 100 gauss). A dome of molten agarose plus particle gelled (crosslinked) at room temperature and sections were made to examine particle arrangements via phase-contrast light microscopy.

Mechanical Property Assessments

The mechanical properties (stiffness) of alginate gels with particles (aligned or non-aligned) at 1 mg/mL, and alginate gels without particles, were assessed by using a custom built device consisting of 2 miniature brushless servo actuators (SMAC, Carlsbad, Calif.), one 50 gram load cell (FUTEK, Irvine, Calif.) with steel plunger having a flat surface for compression and LabVIEW (National Instruments, Austin, Tex.) software for movement control and data acquisition on a laptop.

The gels were placed between two 100 μm thick cover slips and were loaded into the test chamber. The gel height was measured using the internal linear encoder of the SMAC (1 μM resolution). A 5% of original height step compression was applied to the gel subsequently and the force was monitored and recorded. The gel was allowed to equilibrate for 2 minutes and then another 5% step compression was applied. The step compression was applied a total of 4 times, resulting in a net compression of 20%. Using the equilibrium force at each 5% compression level, Young's modulus was calculated (Korhonen et al. (2002). J. Biomech. 35, pp. 903-909).

Cartilage Explant Defects

Osteochondral cores (6 mm), from porcine knees were harvested (OATS system, Arthrex, Naples, Fla.) and cultured in DMEM supplemented with 10% calf serum. Subchondral defects (3 mm wide and 2-3 mm deep) were produced in the center of each core using a 3 mm dermal punch (to define defect size) and scalpel to remove the cartilage. MagN97 labeled chondrocytes or unlabeled cells (control) were mixed in 2% alginate at a density of $8\times10^6$ cells/mL. Prior to crosslinking the alginate in $CaCl_2$ for 10 minutes, some defects were subject to a magnetic field of varying strengths (10-20 gauss) to align or order the cells in vertical columns within the defect. The explants were cultured for one week before being fixed (Z-fix) for 24 hours and placed into 70% ethanol. These plugs were imaged using MRI and then decalcified for histological assessment.

Magnetic Resonance Imaging (MRI)

Fixed osteochondral plugs containing labeled and unlabeled chondrocytes were imaged using both 2D fast spin echo (FSE) imaging and 3D ultrashort TE (UTE) imaging using a 3T Signa TwinSpeed scanner (GE Healthcare Technologies, Milwaukee, Wis.) with a maximum gradient performance of 40 mT/m and 150 mT/m/ms. The 2D FSE sequence employed the following imaging parameters: TR=2000 ms, TE=12 ms, bandwidth=31.25 kHz, echo train length (ETL)=2, FOV=4 cm, slice thickness=0.9 mm, readout=512, phase=320, acquired voxel size=$78\times78\times900$ mm$^3$, NEX=3, scan time=16 minutes. The 3D UTE sequence employed a short hard pulse (40 us in duration) for non-selective excitation, followed by 3D radial ramp sampling with a minimum TE of 8 us. Other imaging parameters included: TR=31 ms, bandwidth=31.25 kHz, FOV=4 cm, readout=384, number of projections=60000, NEX=1, flip angle=9 deg, acquired voxel size=$104\times104\times104$ mm$^3$, scan time=31 minutes.

Example 1

Mammalian Cell Viability in Response to Iron Oxide Particles

Three iron oxide materials were examined:
(i) NanoArc Industrial maghemite ($Fe_2O_3$), 20-40 nm diameter, "NArc";
(ii) Magnetite ($Fe_3O_4$) 97%-325 mesh, ~44 μm diameter, "MagN97" and
(iii) Magnetite ($Fe_3O_4$) 98% 20-30 nm diameter (MagN98).

The iron oxide materials were obtained from the same source (Alfa Aesar, Ward Hill, Mass.). Each particle was weighed and washed in 5 mL absolute ethanol once, centrifuged for 5 minutes at 2000 rpm, washed with 1xPBS three times (5 mL), and finally resuspended in PBS at a weight to volume of 10 mg/mL. Each mixture was sterilized via autoclave.

Human articular cartilage was obtained from tissue banks (see above). Chondrocytes were isolated via enzymatic digestion and cultured for one passage.

Specifically, human chondrocytes were seeded in 96-well plates (5000 cells per well) and precultured overnight in DMEM with 2% calf serum. Following pre-culture, the cells were exposed to 0.01, 0.1 and 1 mg/mL of each particle type (NArc, MagN97, MagN98) for 72 hours, by introducing particle suspensions into the cell culture medium.

MTT Assay

The MTT colorimetric assay was used to determine potential toxicity and cell viability of each iron oxide particle type. MTT is reduced by metabolically active cells to insoluble purple formazan dye crystals. The rate of reduction is proportional to the rate of cell proliferation, and therefore, proportional to the amount of live cells in the culture.

Briefly, human chondrocytes were ceded in 96-well plates (5000 cells per well) and pre-cultured overnight in DMEM with 2% calf serum. Following pre-culture, the cells were exposed to 0.01, 0.1 and 1 mg/mL of each particle type for 72 hours.

Cell culture medium was aspirated, new medium added, and MTT was added to the wells and the cells were incubated for 6 hours. Assessment of cell viability was conducted via microplate reader at 540 nm, with a higher optical density (OD) correlated with cell death.

Figure 2:
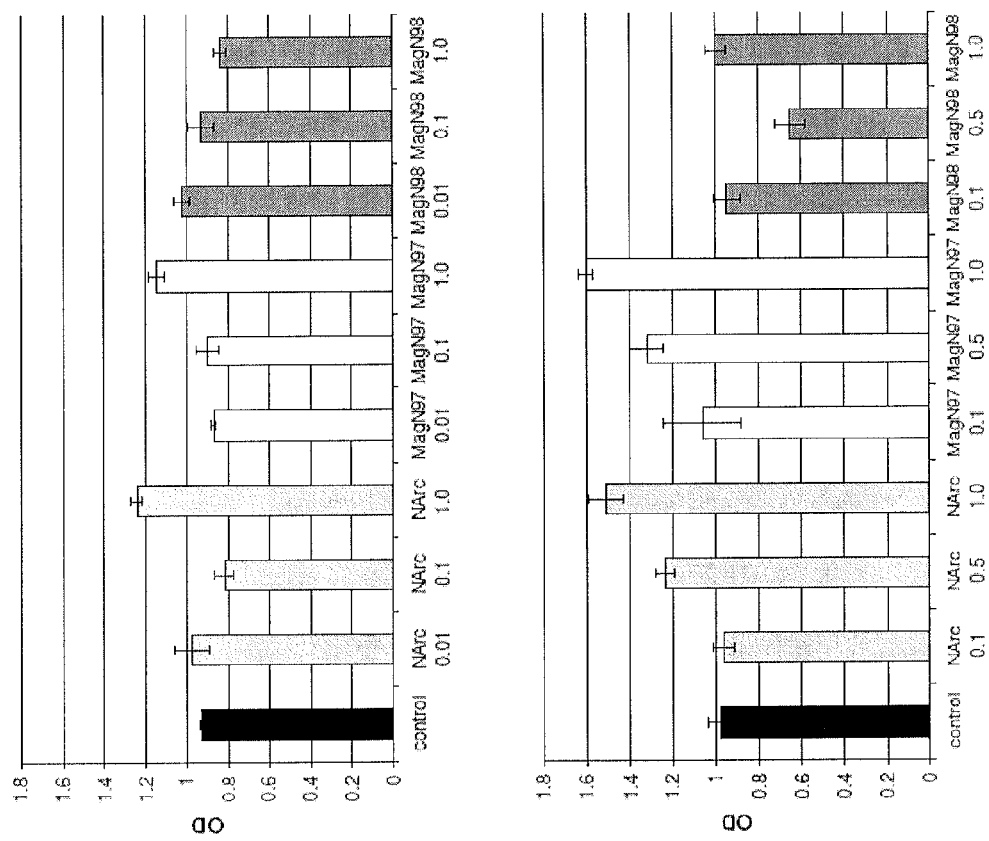
FIG. 2 shows the results of a chondrocyte viability MTT ((3-[4,5-dimethylthiazol-2-yl]-2,5-diphenyltetrazolium bromide) assay.
Top: Graph showing the optical density in the MTT assay versus cell treatment group.
Bottom: Results of a long term viability assay with cells stored in phosphate-buffered saline (PBS) for 9 months, plotted as optical density in the MTT assay versus cell treatment group.

Following exposure to iron oxide particles for 72 hours, as compared to controls, a significant shift in OD measurements was not observed for each particle at 0.01, 0.1 and 1 mg/mL (FIG. 2, top). A shift in OD indicates cell death has occurred.

Increased OD in NArc (1 mg/mL) was likely due to the red color of these particles.

For longer-term assessments, human chondrocytes ($8\times10^6$ cells/mL) were embedded in alginate with 0.1, 0.5 and 1 mg/mL of each particle for 72 hours, and cultured in chondrogenic medium for 2 weeks. Prior to incubation with the cells, the particles had been stored for 9 months in PBS at 4° C.

Long Term Assessment

Iron oxide particles were stored in PBS at 4° C. for 9 months to study whether the particles release toxic materials. Chondrocyte cell cultures were exposed to each iron oxide particle (at concentrations of 0.1, 0.5 and 1 mg/mL) for 72 hours, and cultured for two weeks. There was no significant increase in OD when subjected to the MTT assay, indicating no release of toxic materials over time (FIG. 2, bottom).

Figure 3:
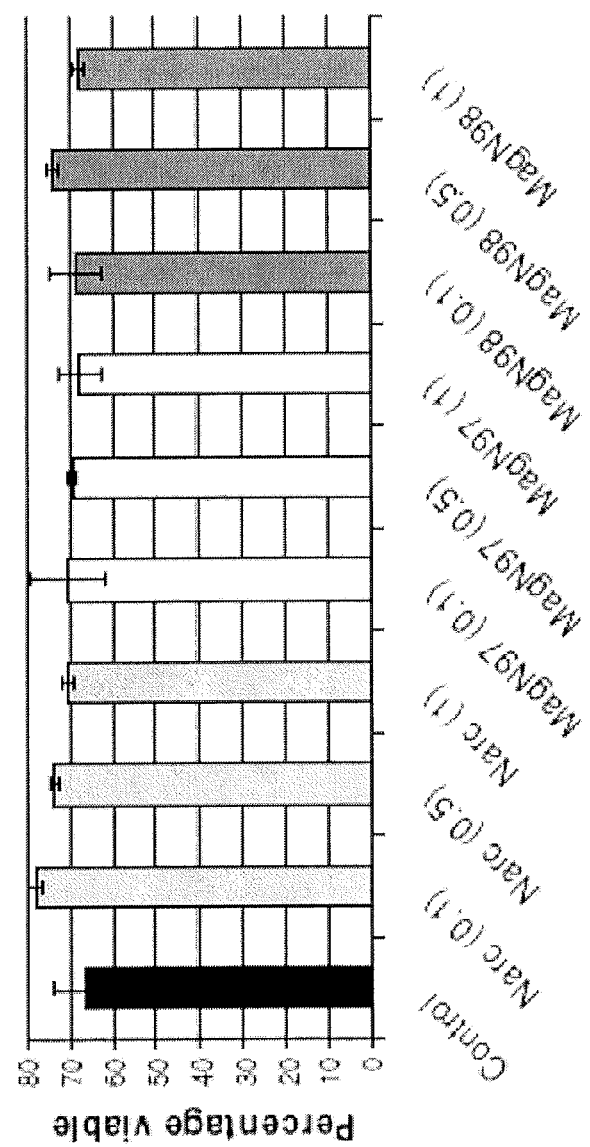
FIG. 3 is a graph showing the percentage chondrocyte viability calculated from confocal images of chondrocyte-alginate cultures subjected to 0.1, 0.5 and 1 mg/mL of each iron oxide particle for 72 hours, followed by cell culture for 14 days.

Different cell cultures were subjected to the same 72 hour treatment, cultured for two weeks and stored in PBS 4° C. for 9 months. Cells were then stained with calcein AM and ethidium homodimer-1. These live/dead assays were used to confirm the non-significant effect of iron oxide particles on viability, as reported by the MTT assays. FIG. 3 shows the results of the study.

Live/dead staining (calcein-AM and ethidium homodimer-1) was performed as reported by Grogan et al. using confocal microscopy (LSM 510, Zeiss, Hamburg, Germany) (Grogan et al. (2003). J. Pathol. 198, pp. 5-13).

The number of live cells was assessed using an image analysis script written in MATLAB (MathWorks, Natick, Mass.). Viability was reported as percentage of live cells.

The maghemite particle NArc and two magnetite ($Fe_3O_4$) particles MagN97 and MagN98 did not show an adverse effect on chondrocyte viability when mixed and cultured in alginate over several weeks. Additionally, neither a release of toxins nor a change in cell viability was detected using iron oxide particles stored over this time period (FIG. 3).

Specifically, FIG. 3 shows the percentage chondrocyte viability calculated from confocal images of alginate cultures subjected to 0.1, 0.5 and 1 mg/mL of each iron oxide particle. The results show that cells cultured with the iron oxide particles were as viable as control cells.

Example 2

Evaluation of Gene Expression in Human Chondrocytes Mixed With Iron Oxide Particles Human chondrocyte pellets cultures ($5\times10^5$ cells each) were formed in the presence of iron oxide particles (1 mg/mL).

Three species of iron oxide particles were tested separately:

(i) NanoArc industrial maghemite ($Fe_2O_3$), 20-40 nm (NArc);
(ii) Magnetite ($Fe_3O_4$) 97%-325 mesh (~44 μm) (MagN97) and
(iii) Magnetite ($Fe_3O_4$) 98% 20-30 nm (MagN98).

Cell pellet cultures were maintained in serum-free ITS+ medium supplemented with TGFβ1 (10 ng/mL), for 12 days (as described by Barber et al. (2004). Osteoarthritis Cartilage 12, pp. 476-484). The medium was changed every 3 days. After 12 days, some pellets were fixed and embedded in paraffin for histology, while other pellets were prepared for RNA extraction for gene expression analysis.

Gene Expression Analysis

Cells were harvested, and total RNA was isolated from the cultured cell pellets, using the RNAeasy mini kit (Qiagen, Hilden, Germany). First strand cDNA synthesis was performed using total RNA as a template according to the manufacturer's protocols (Applied Biosystems, Foster City, Calif.). Quantitative real time PCR was performed using TaqMan® gene expression reagents.

Magnetically-labeled cells were probed for expression of the following genes: GAPDH, COL1A1, COL2A1, COL10A1 and AGGRECAN (AGG).

Figure 4:
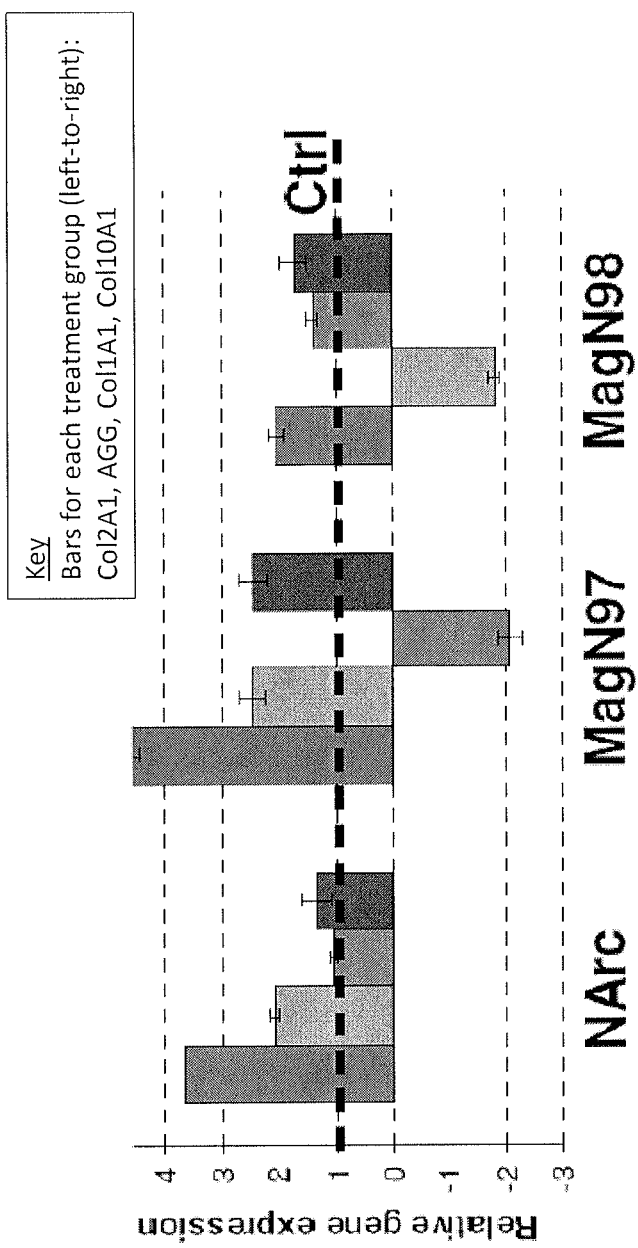
FIG. 4 is a graph showing the fold change in mRNA expression levels of Col2A1, AGG, Col1A1 and Col10A1, relative to control, in 12 day cultivated pellet cultures in the presence of 1 mg/mL NArc, 1 mg/mL MagN97 or 1 mg/mL MagN98. The data in for each treatment group is arranged from left to right as follows: Col2A1, AGG, Col1A1 and Col10A1.

GAPDH, COL1A1, COL2A1, COL10A1 and AGGRECAN (AGG) were detected using Assays-on-Demand™ primer/probe sets (Applied Biosystems, Foster City, Calif.). Expression levels were normalized to GAPDH using the recommended ΔCt method, and fold-change was calculated using the $2^{-\Delta\Delta CT}$ formula. The results of the study are presented in graphical format, and separated by treatment group (i.e., particle type) (FIG. 4). Data is arranged from left-to-right in FIG. 4, for each treatment group, as follows: (Col2A1, AGG, Col1A1, Col10A1)

Two particles tested (NArc and MagN97) enhanced mRNA expression of two major cartilage-associated genes (Col2A1 and AGG), during tissue formation, as compared to control pellets (FIG. 4). MagN97 pellets show a 2-fold increase in Col10a1. Although a 2-fold increase in Col2a1 was detected in MagN98 pellets, a reduced AGG mRNA expression level was observed.

Histology and Neocartilage Grading (Bern Score)

12-day old pellets were fixed in Z-Fix (ANATECH, Battle Creek, Mich.) and paraffin embedded. Sections of 4-5 μm were made for Safranin O-fast green staining. Immunohistochemical (IHC) analyses of collagen type II was performed using conditions previously described (Grogan et al. (2009). Arthritis Res. Ther. 11, p. R85). Neocartilage quality was assessed (two observers) using the Bern Score (Grogan et al. (2006). Tissue Eng. 12, pp. 2141-2149), which assesses the intensity of Safranin O stain, distance between cells or the amount of extracellular matrix produced and cell morphology.

The high-density cultures produced discs of neocartilage tissue in all magnetic particle treatments over two weeks in culture. Further, each disk could be moved or levitated by an external magnet. Each disc was cut in half for gene expression analysis or fixed for histology.

Figure 5:
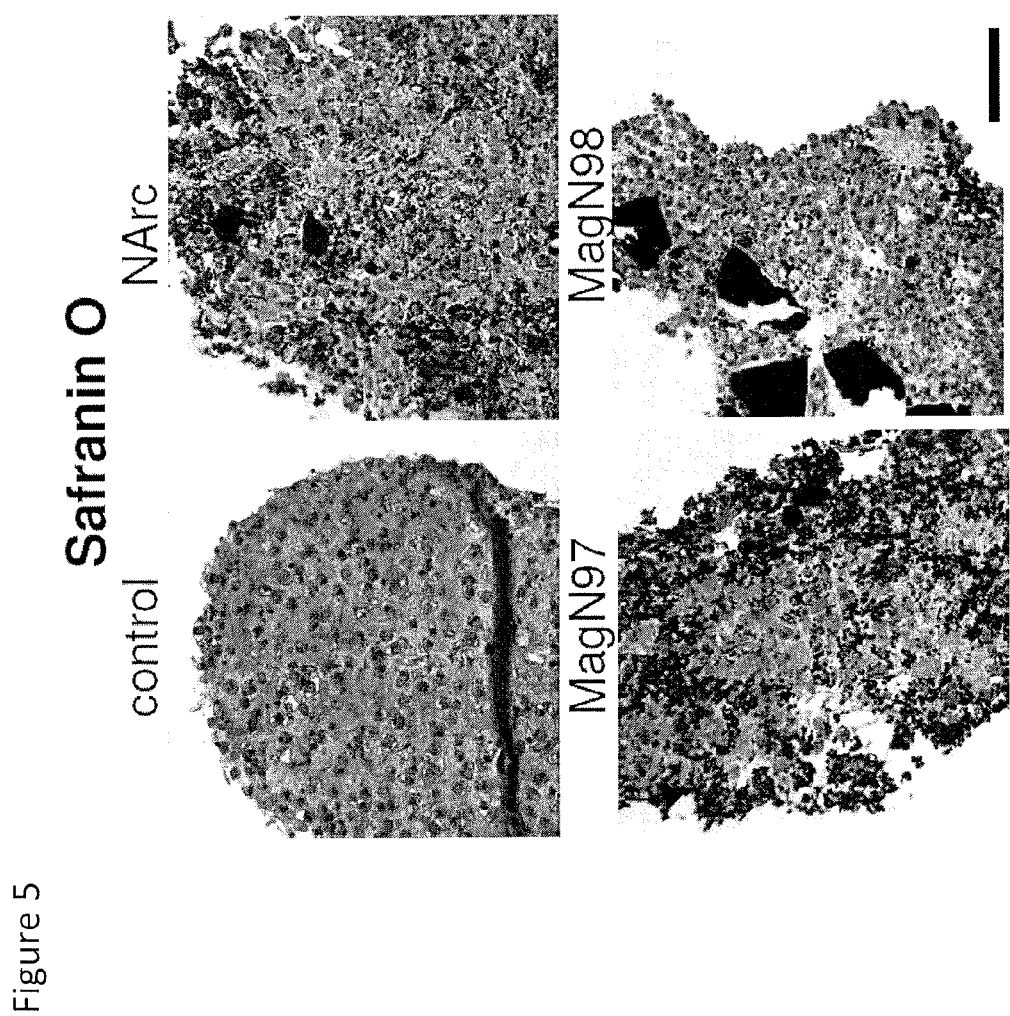
FIG. 5 is an image of a Safranin O stained pellet cultures in the presence of 1 mg/mL NArc, 1 mg/mL MagN97 or 1 mg/mL MagN98 (scale bar 50 μm).
Figure 6:
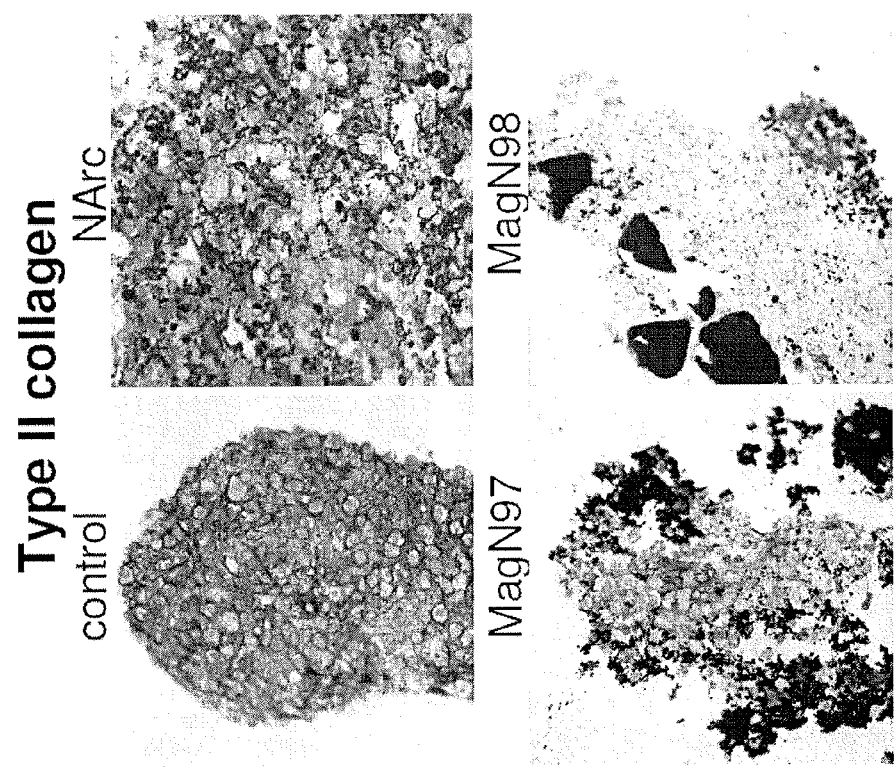
FIG. 6 are images of a Safranin O stained pellet cultures in the presence of 1 mg/mL NArc, 1 mg/mL MagN97 or 1 mg/mL MagN98, to visualize type II collagen deposition.

Cells treated with NArc and MagN97 displayed comparable glycosaminoglycan (GAG) staining levels (Safranin O, FIG. 5, Bern scores: control=7.8±0.3, NArc=7.3±0.3, MagN97=6.5±0.5 and MagN98=3.5±0.5) and collagen type II levels (FIG. 6).

Example 3

Evaluation of Gene Expression in High Density Magnetically-Labeled Chondrocyte-Alginate Cultures Human chondrocytes were incubated with MagN97, MagN98 or NArc (1 mg/mL) for 24 hours. Particles rapidly adhered to cells within 30-40 minutes and some particles were engulfed by the cells over 24 hours. Following removal of excess particles by washing in PBS, the cells were detached, mixed into 2% alginate, and transferred into cell-culture inserts, and cultured for two weeks (FIG. 1). The cultures were developed using $2 \times 10^6$ cells.

Three species of iron oxide particles (1 mg/mL) were tested separately.

Gene Expression Analysis

Cells were harvested and total RNA was isolated from the isolated cells using the RNAeasy mini kit (Qiagen, Hilden, Germany). First strand cDNA synthesis was performed using total RNA as a template according to the manufacturer's protocols (Applied Biosystems, Foster City, Calif.). Quantitative real time PCR was performed using TagMan® gene expression reagents. GAPDH, COL2A1, COL10A1 and AGGRECAN (AGG) were detected using Assays-on-Demand™ primer/probe sets (Applied Biosystems, Foster City, Calif.). Expression levels were normalized to GAPDH using the recommended ΔCt method, and fold-change was calculated using the $2^{-\Delta\Delta CT}$ formula.

Figure 7:
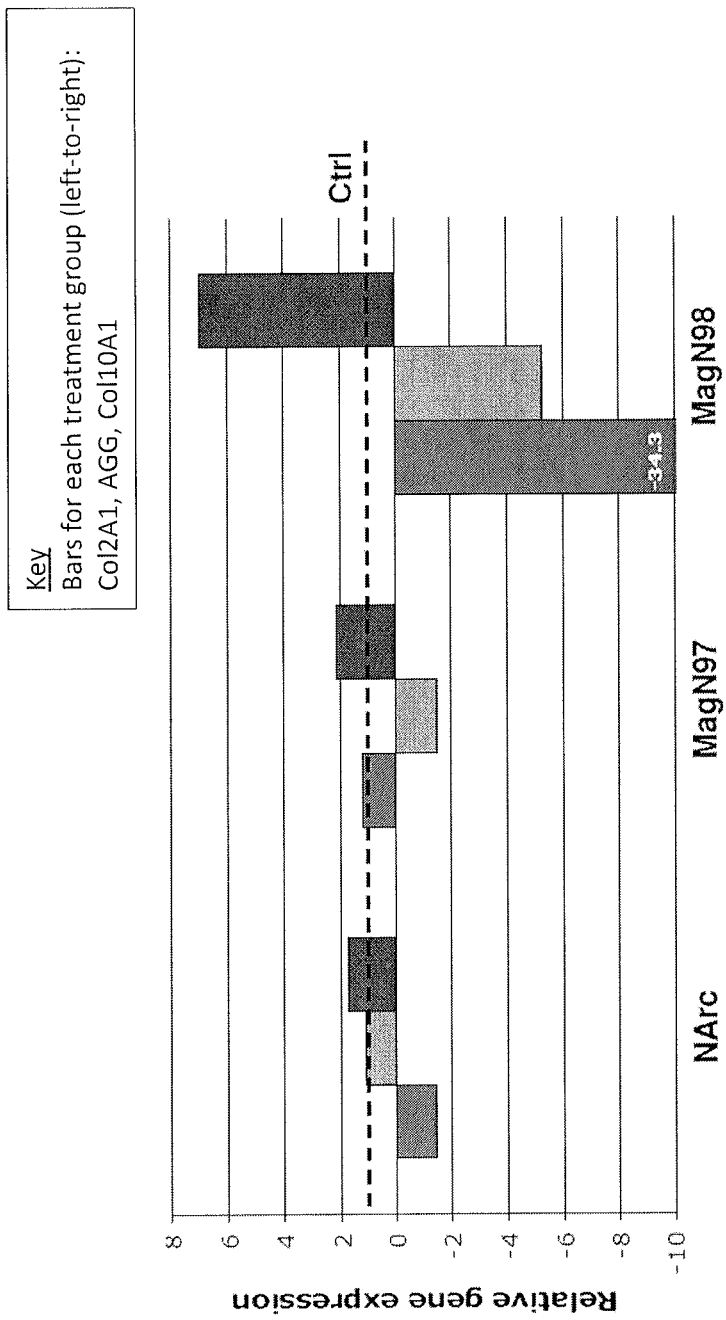
FIG. 7 is a graph showing the fold change in mRNA expression levels of Col2A1, AGG and Col10A1, relative to control (GAPDH), in neocartilage formed by one method of the present invention. The data is arranged from left to right for each treatment group as follows: Col2A1, AGG and Col10A1.

The NArc and MagN97 treated cultures exhibited no significant change in gene expression in the three genes tested (COL2A1, COL10A1 and AGG) (FIG. 7). In contrast, the cultures treated with MagN98 exhibited a significant decrease in both COL2A1 and AGG mRNA levels, and also exhibited a significant increase in Col10A1 levels, as compared to control.

Histology—Cell Staining with Safranin O

High-density cultures, developed in the cell culture insert system using $2 \times 10^6$ cells, produced discs of neocartilage tissue in all treatments over 2 weeks in culture. Each disc was cut in half for either gene expression analysis or fixed for histology. Discs were cut in half and fixed for histology in Z-Fix (ANATECH, Battle Creek, Mich.) and paraffin embedded. Sections of 4-5 μm were made for Safranin O-fast green staining.

Figure 8:
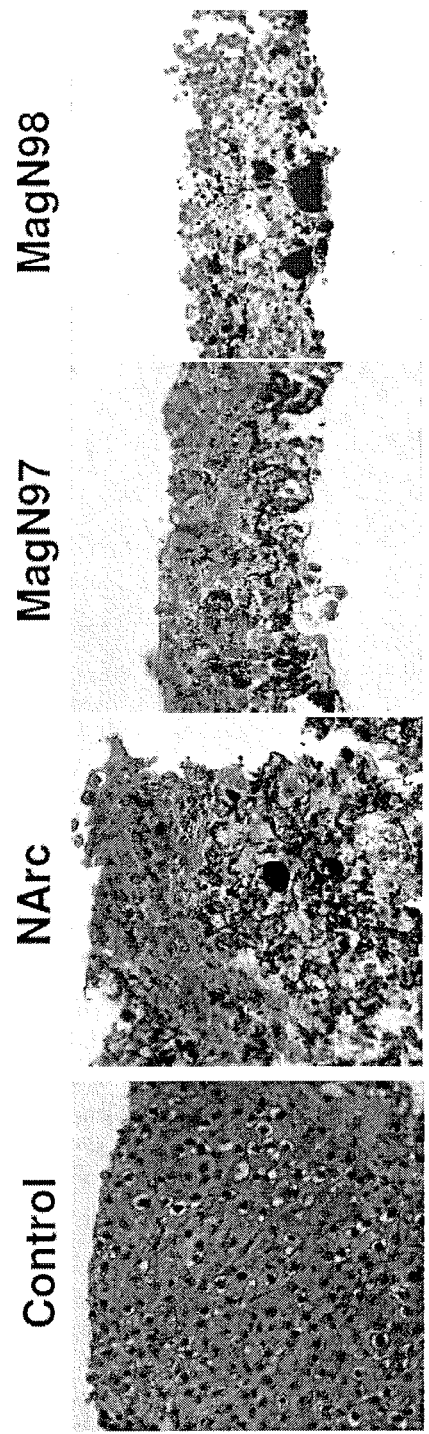
FIG. 8 are images of neocartilage formed by one method of the present invention, stained with Safranin O.

Cartilage appears red after Safranin O staining, and the NArc and MAGN97 groups were stained to a greater extent than the MagN98 group (FIG. 8). Staining indicated comparable cartilaginous extracellular matrix production in NArc and MagN97 pellets in relation to control. MagN98 appeared to prevent normal GAG deposition.

Example 4

Alignment/Ordering of Human Chondrocytes Into Multiple Orientations

Labeled human chondrocytes were arranged into distinct patterns in alginate hydrogel before crosslinking in calcium chloride.

Chondrocytes were seeded in monolayer culture at a density of $50 \times 10^3$ cells per cm² and cultured for 24 hours.

Human chondrocytes were incubated with either MagN97 (1 mg/mL) or NArc (1 mg/mL) for 2 hours. These particles adhered to cells within 30-40 minutes. Cells were then washed with PBS, detached, mixed with 2% alginate solution at a density of 8×10⁶/mL, and transferred into a cell-culture insert (8 nm; BD Biosciences, San Jose, Calif.).

The cell culture insert was placed in a $CaCl_2$ bath, as shown in FIG. 1.

Figure 9:
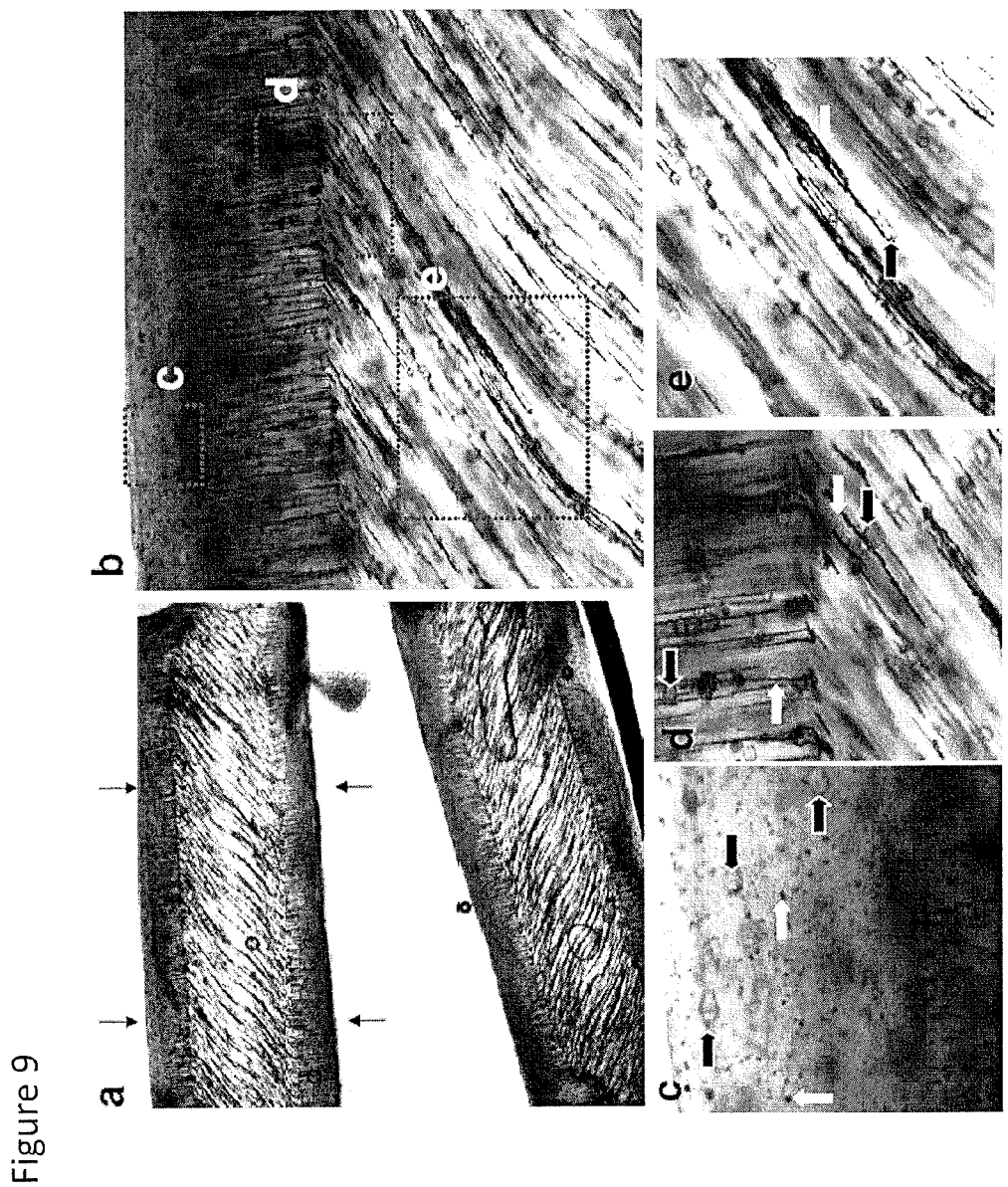
FIG. 9 shows images of various arrangements of MagN97 labeled cells in crosslinked alginate hydrogels.
Figure 10:
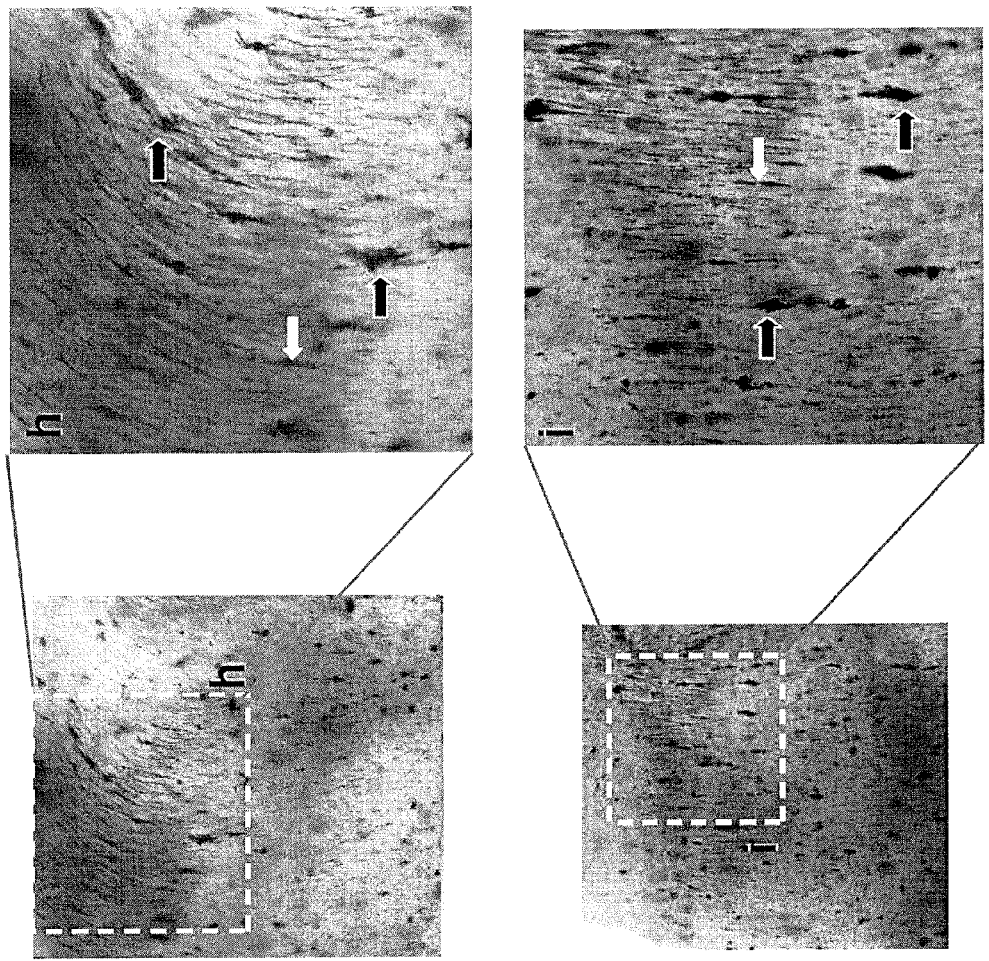
FIG. 10 shows images of various arrangements of NArc (1 mg/mL) labeled cells in crosslinked alginate hydrogels.

A magnet was then positioned below the $CaCl_2$ bath for 2 minutes, in order to align the cells and particles into vertical columns. After 2 minutes, the magnet was repositioned to 90 degrees (perpendicular to the original orientation) for the remaining gelling time (20-30 minutes) to produce multi-cell/particle arrangements (FIGS. 9, 10). During this time, $CaCl_2$ solution was carefully added into the insert to affect crosslinking in both directions. Results from MagN97 particle experiments are shown in FIGS. 9a-9e, while results from NArc particle experiments are shown in FIG. 10.

FIG. 9a (light microscopy image is magnified 2×) shows the results of one experiment. As described above, the alginate hydrogel was crosslinked in two directions by first aligning the cells vertically with a magnetic field, followed by moving the magnet 90°, to move the cells in a diagonal arrangement.

FIG. 9b is a magnified image (40×) of the FIG. 9a image (2×), showing three regional arrangements of cells and particles in a hydrogel subjected to two magnetic fields, which were perpendicular to one another and applied serially, as described above. FIGS. 9c, 9d and 9e are selected insets taken from FIG. 9b. FIG. 9c shows that cells (bold black arrows) and particles (bold white arrows) on the surface of the hydrogel are not organized. FIG. 9d is a region showing a transition between a vertical alignment and a diagonal arrangement. Finally, FIG. 9e shows alignment of cells as a consequence of interaction with the magnetically aligned particles.

FIG. 10 shows images (top-left, bottm-left images: 10× magnification) of NArc labeled chondrocytes in 2% alginate. FIG. 10 (top) shows NArc labeled cells organized in a curved arrangement, while FIG. 10 (bottom), shows NArc labeled cells arranged in parallel arrangement. Black arrows point to cells while white arrows point to particles.

Example 5

Alignment of Iron Oxide Particles in Alginate and Agarose Hydrogels

Particle organizations with alginate and agarose hydrogels were formed by mixing MagN97 (5 mg/mL) or NArc (5 mg/mL) particle suspensions with (1) 2% alginate or (2) low melting point agarose. Mixtures were then transferred to cell culture inserts, and the mixtures in each cell culture insert solidified either at room temperature (in the presence or absence of a magnetic field), or in a calcium chloride bath (in the presence or absence of a magnetic field).

Figure 11:
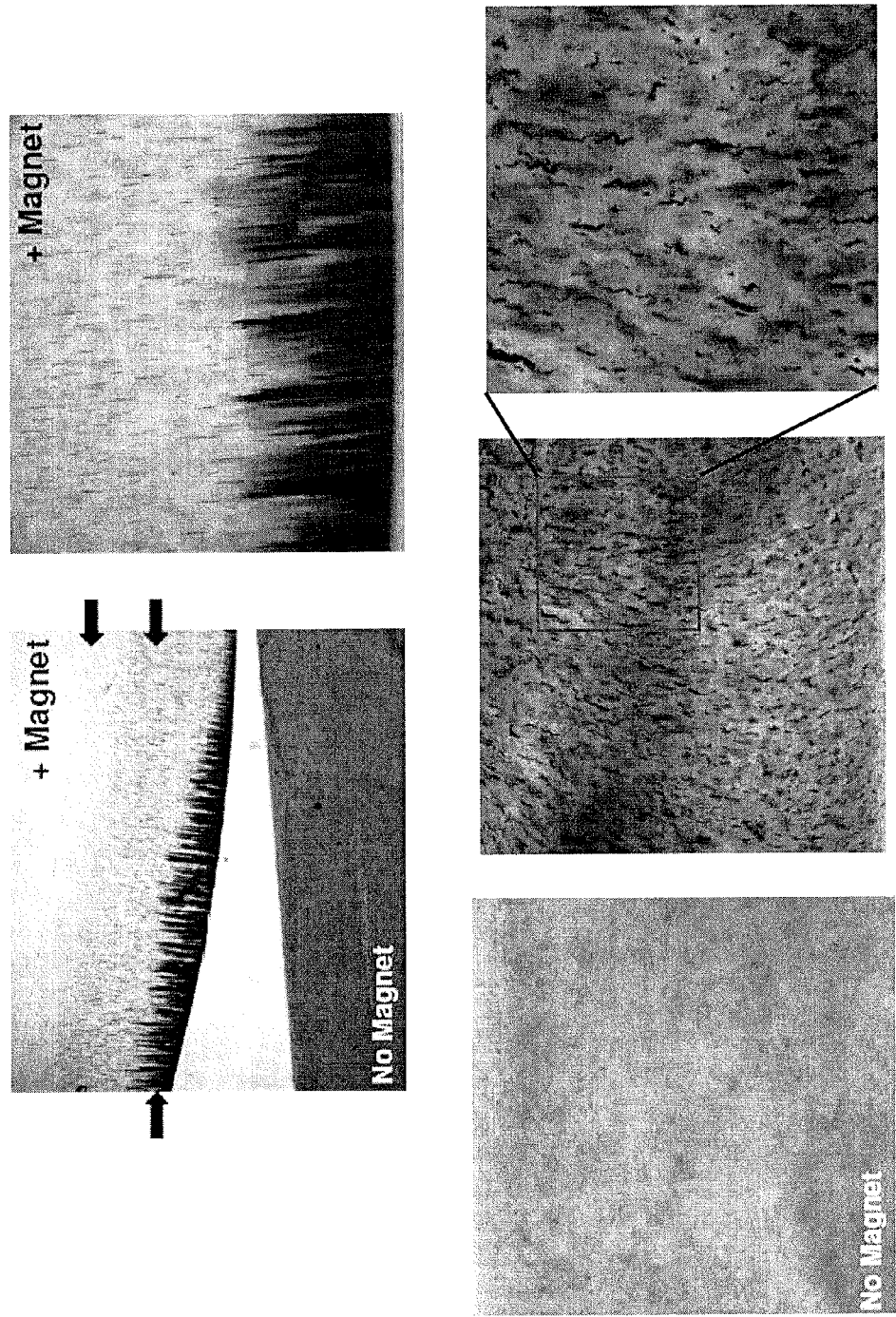
FIG. 11 shows images of various iron oxide particle arrangements in crosslinked hydrogels. MagN97 (5 mg/mL) mixed in low melting point agarose (40° C.) and permitted to solidify at room temperature in the presence or absence of magnetic filed (top-left, magnification 2×). Top-right: higher magnification (10×) of MagN97 pattern.
Bottom-left: NArc (5 mg/mL) in alginate without a magnetic field.
Bottom-middle: NArc in the presence of a magnetic field under the same conditions described for MagN97 (10× magnification).

The particle patterns shown in FIG. 11 were formed in agarose. The particles are added to hot-liquid agarose (approximately 45° C.) and then pipetted onto a plastic surface. While still warm and in the liquid state, the particles were either aligned with a magnetic field below or above the agarose-particle mix (alternatively, no magnetic field was applied). Once the agarose solidified at room temperature, the magnets were removed.

Vertically oriented MagN97 particles are presented in the top row of images in FIG. 11.

Phase contrast images of NArc particles in crosslinked agarose hydrogel are provided in FIG. 11, bottom. FIG. 11 (bottom, left) shows the crosslinked agarose hydrogel with NArc particles, without a magnetic field. FIG. 11 (bottom, middle) shows a phase contrast image of a crosslinked hydrogel with NArc particles, when a magnetic field was applied during crosslinking to the particle-hydrogel mixture. FIG. 11 (bottom, right) is an inset of a portion of the image shown in FIG. 11 (bottom, middle).

Figure 12:
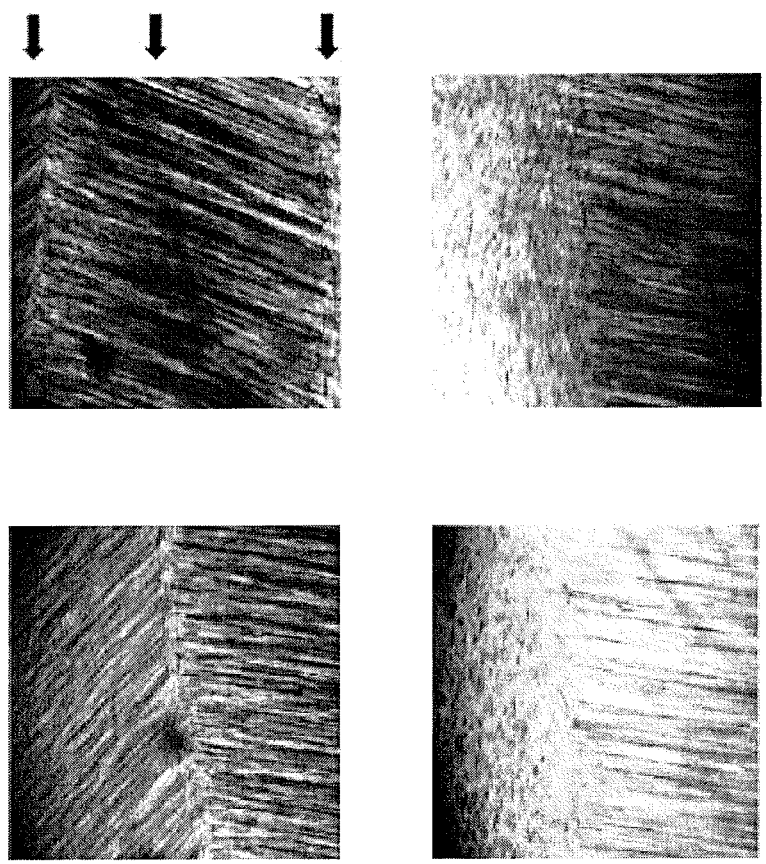
FIG. 12 shows images of MagN97 (5 mg/mL) arrangements in crosslinked 2% alginate hydrogels, created in a gradient of $CaCl_2$ and movement of an external magnetic field orientation during crosslinking.
Top-left: depicting a feather organization.
Top-right: three different arrangements within one gel (indicated by black arrows).
Bottom: Both images show two distinct adjacent patterns that are approximately 90° different.

Multiple directional arrangements of MagN97 particles in 2% alginate were created by placing the hydrogel-particle mixture in a gradient of $CaCl_2$ and by moving the external magnetic field orientation during the crosslinking. FIG. 12 (top-left), is a phase contrast image the particles in a "feather" arrangement in the crosslinked 2% alginate hydrogel. Multiple arrangements in a single hydrogel were also formed. FIG. 12 (top-right) is a phase contrast image the MagN97 particles in three different orientations in the crosslinked 2% alginate hydrogel (arrows in the figure indicate different orientations).

MagN97 particles were also manipulated in 2% alginate, to form adjacent patterns that were approximately 90° different, by rotating the external magnetic field 90°. FIG. 12 (bottom-left) and FIG. 12 (bottom-right) are phase contrast images of these particle orientations.

Example 6

Alignment of Iron Oxide Particles in Agarose Hydrogels

Three iron oxide materials were examined:
(i) NanoArc Industrial maghemite ($Fe_2O_3$), 20-40 nm diameter, "NArc";
(ii) Magnetite ($Fe_3O_4$) 97%-325 mesh, ~44 μm diameter, "MagN97" and
(iii) Magnetite ($Fe_3O_4$) 98% 20-30 nm diameter (MagN98).

The iron oxide materials were obtained from the same source (Alfa Aesar, Ward Hill, Mass.). Each particle was weighed and washed in 5 mL absolute ethanol once, centrifuged for 5 minutes at 2000 rpm, washed with PBS three times (5 mL), and finally resuspended in phosphate-buffered saline (PBS) at a weight to volume of 10 mg/mL. Each mixture was sterilized via autoclave.

Each particle was suspended at 5 mg/mL in 1% low melting point agarose in the presence or absence of a magnetic field (approx. 100 gauss). A dome of molten agarose+particle was allowed to gel at room temperature and sections were made to examine particle arrangements via phase contrast light microscopy.

Multiple arrangements of iron oxide particles produced in agarose and alginate in the presence of a magnetic field. All images in FIG. 13 were of iron oxide particles (5 mg/mL) suspended in 1% agarose.

Figure 13:
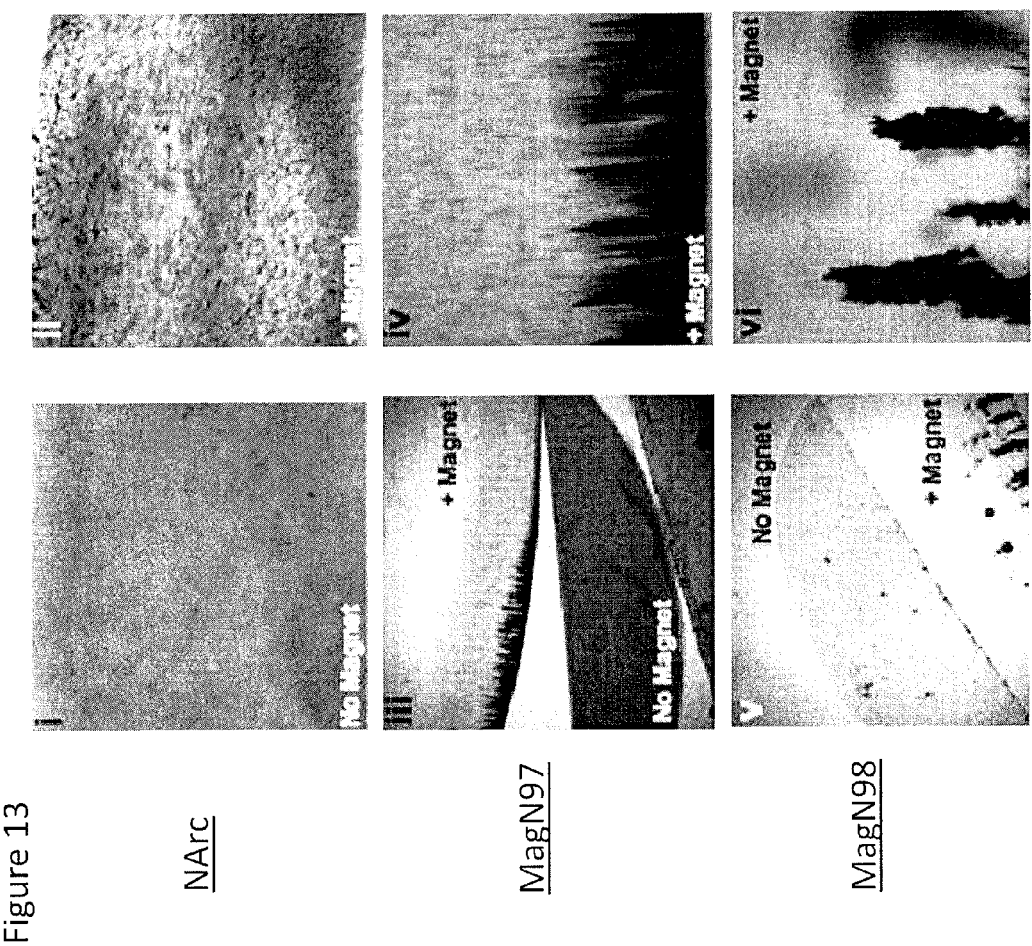
FIG. 13 shows images of various iron oxide particle (5 mg/mL) arrangements in crosslinked agarose hydrogels.
Top: NArc particles in the absence (left) and presence (right) of a magnetic field (magnification 10×).
Middle: MagN97 particles in the presence and absence of magnetic field. Magnification 2× (left) and 10× (right).
Bottom: MagN98 particles at magnification 2× (left) and 10× (right).

The top left image in FIG. 13 shows an NArc containing hydrogel in the absence of a magnetic field (magnification 10×). The top right image in FIG. 13 shows an NArc containing hydrogel in the presence of a magnetic field (magnification 10×)

The left image in the middle row of FIG. 13 shows patterns of MagN97 particles formed in agarose hydrogel with and without magnetic fields (magnification 2×).

The right image in the middle row of FIG. 13 shows MagN97 alignment (mag. 10×) in an agarose hydrogel.

The bottom left and right images of FIG. 13 show an agarose hydrogel having MagN98 patterns (mag. 2×) (bottom left) and MagN98 (mag. 40×) (bottom right).

Example 7

Modeling of Magnetic Fields in Hydrogels

To determine a specific arrangement of magnets to provide a given magnetic field shape, commercially available software was used (Vizimag® release 3.193, Vizimag.com).

Figure 14:
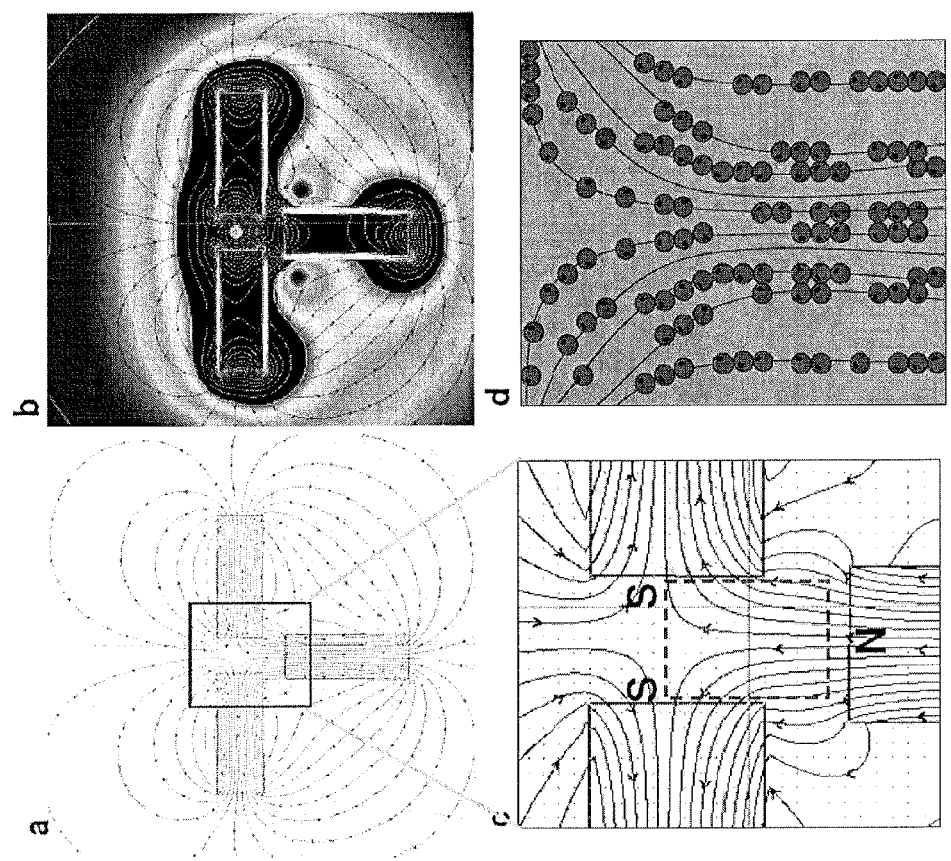
FIG. 14 show images of a theoretical magnetic field shape and density using three magnets, and a predicted arrangement of iron oxide labeled cells in 2% alginate using modeled magnetic fields in the three magnet configuration.

A theoretical magnetic field shape using three magnets provided a region that simulated the type of cell arrangement that somewhat emulated articular cartilage cell arrangement of deep zone columns and tangential superficial zone cell alignment (FIG. 14).

Magnetic fields were modeled to determine if more intricate cellular arrangements/particle arrangements could be made in a hydrogel of the invention. The modeling of magnetic fields indicated that complicated cellular arrangements are possible. FIG. 14a shows the shape of the field and FIG. 14b shows the density map of the same theoretical field. FIG. 14c is an inset of the theoretical magnetic field shape shown in FIG. 14a.

Based on the magnetic field mapping and the results shown in FIGS. 14a-14c, the arrangement of iron oxide labeled cells in 2% alginate was predicted. The predicted arrangement of the labeled cells is presented in FIG. 14d.

Figure 15:
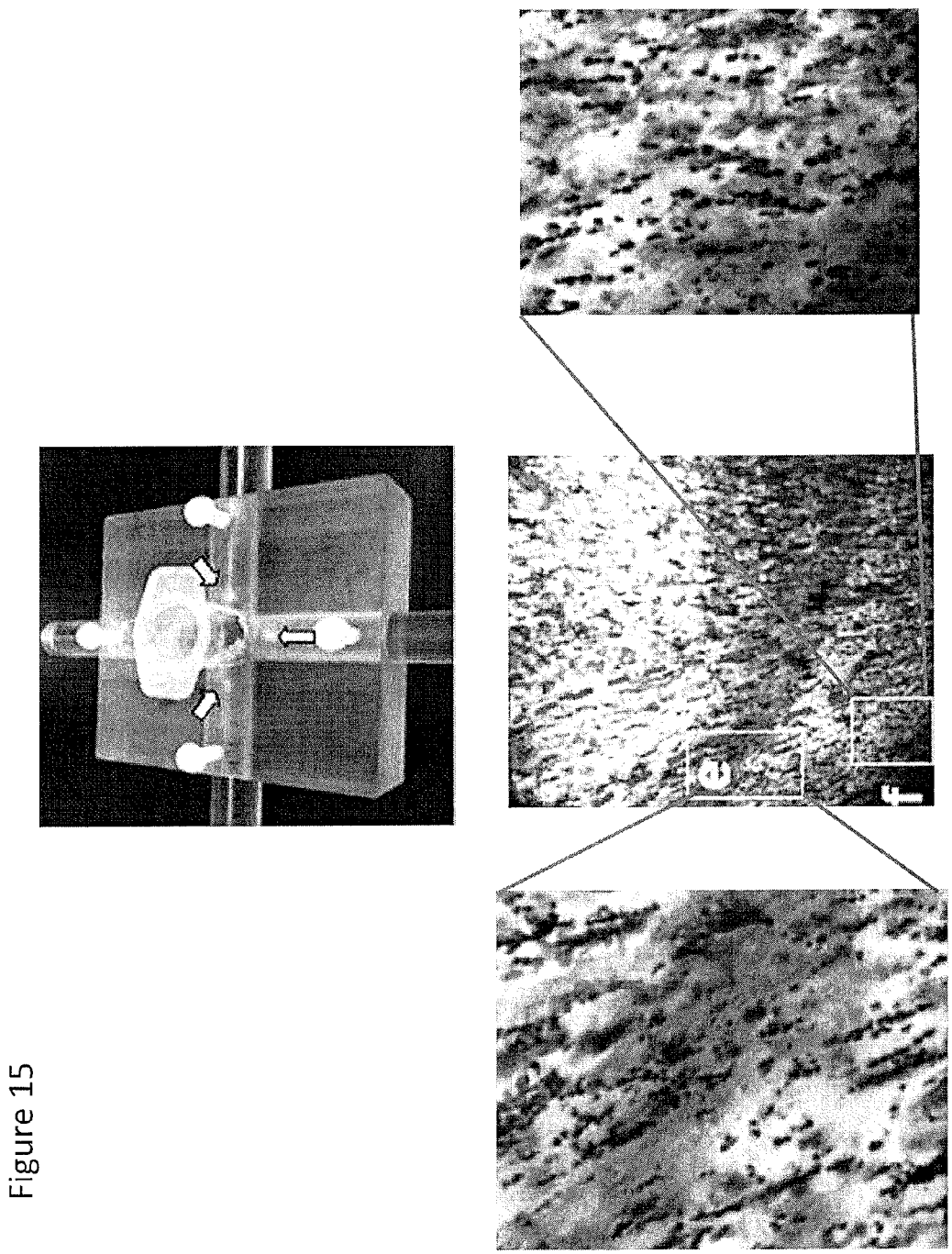
FIG. 15 shows a device to hold three magnet configuration (white arrows indicate magnets) with a central well with cells in alginate (top). Production of curved-labeled cells with the three magnet setup using MagN97 (1 mg/mL) (bottom-middle, magnification 10×). The bottom-left image is an inset of the bottom-middle showing a diagonal arrangement. The bottom-right image is an inset of the bottom-middle image showing vertical cell and particle arrangements in the same gel.

A custom made device was used to house three magnets in the predetermined configuration, with central well to place labeled cells in 2% alginate for alignment before crosslinking (FIG. 15, top). The white arrows indicate the magnet positions.

Production of curved-labeled cells with the three magnet setup using MagN97 (1 mg/ml) is shown in the bottom-middle image (10× magnification) of FIG. 15. The bottom-left image is an inset of the bottom-middle image with diagonal arrangement of particles. The bottom-right image is an inset of the bottom-middle image with vertical cell and particle arrangements.

Example 8

Fusion of Pre-aligned Crosslinked Alginate Hydrogels

Fusing hydrogels together may be beneficial as the formation of multiple arrangements in a single hydrogel generated a "hinge" effect, which is a result of the particles aligning and forming strands that are not easily disrupted, even following a change in the magnetic field orientation.

Discrete hydrogel layers, each with a unique cellular arrangement, were fused together in order to generate a more complex three dimensional hydrogel architecture. The individual hydrogels were already crosslinked at the time of fusion. Two different alginate hydrogels were produced. Each contained MagN97 particles as were formed as indicated above. One gel comprised cells that were pre-labeled with CSFE dye prior to MagN97 attachment. CSFE allowed for visualization of the cells after gel fusion, and was used to demark the interface region of the cells.

Prior to fusion, as described in greater detail, above, non-stained and CSFE stained (green) MagN97 labeled chondrocytes were separately mixed in 2% alginate, separately aligned using a magnetic field and crosslinked to form the two discrete hydrogels.

To fuse both gels, one surface of the CSFE gel was exposed to filter paper soaked with a chelating solution of sodium citrate (82 mM) in 4 mg/mL, non-crosslinked alginate for 2 minutes at room temperature, to partially dissolve the surface. Following removal of the filter paper, the non-CSFE labeled gel with a different MagN97 particle/cell alignment was immediately placed on the treated surface for a further 8 minutes. The sample (hydrogel-hydrogel composition) was then maintained in a $CaCl_2$ solution (80 mM CaCl2, 49 mM NaCl, 25 mM HEPES) for 15 minutes to crosslink the alginate gels at the partially dissolved interface.

Figure 16:
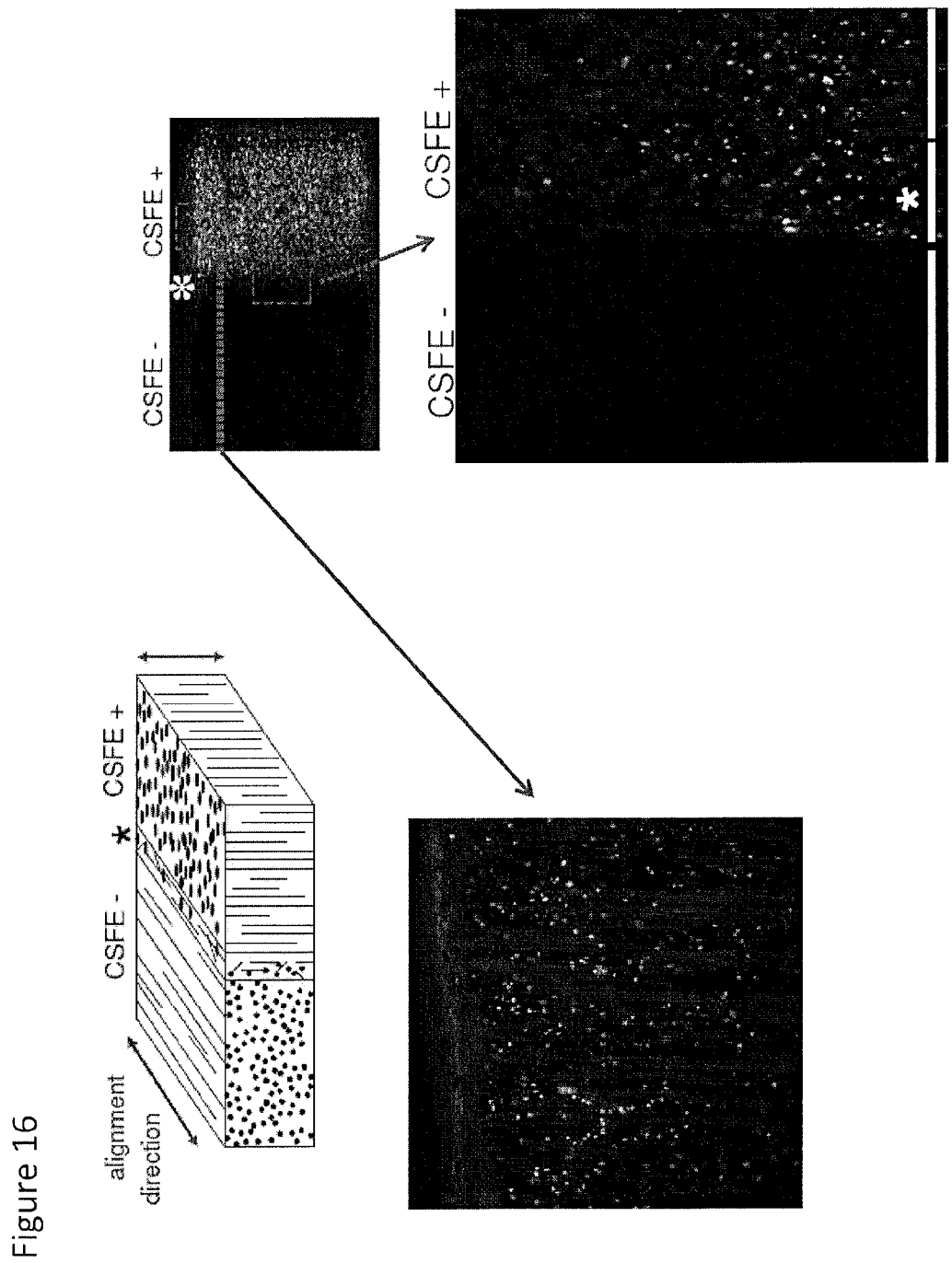
FIG. 16 is an image of two alginate gels with different magnetic particle organizations fused together. Cells in one hydrogel were labeled with CSFE (right) and cells in the other hydrogel were not labeled (left).

Hoechst 33342 was used to visualize cells in both gels. FIG. 16 (top, left) is a diagram depicting the orientation of cell and MagN97 alignment and the interface region of the fused gels (denoted by an asterisk).

FIG. 16 (top-right) shows a fluorescent image of the fused gels, where CSFE fluorescence is visualized. FIG. 16 (bottom-right) shows the interface, but at a higher magnification. FIG. 16 (bottom-left) is an image of the Hoeshst 33342 stained hydrogel containing CSFE labeled cells, which shows columnar arrangements of MagN97 magnetically-labeled cells.

Microscopic examination of fused hydrogels revealed the interface regions and the distinct CSFE positive and negative portions, as well as particle orientation (FIG. 16).

Figure 17:
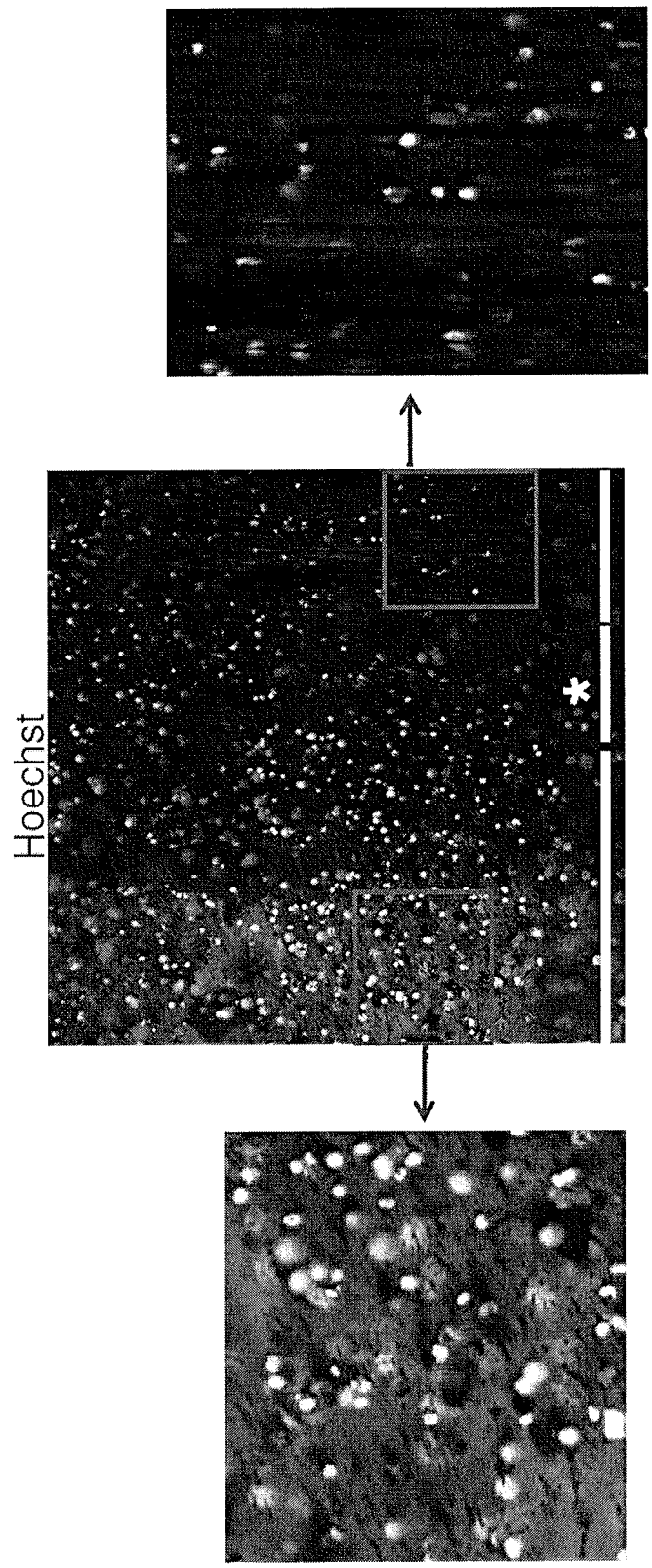
FIG. 17 (middle) is an image of the fused hydrogel, after staining with Hoechst 33342 to show the locality of cells in both gels. The left and right images are higher magnification images of the image shown in FIG. 17 (middle). The asterisk signifies the fusion interface.

FIG. 17 (middle) is an image of the Hoechst 33342 staining showing the locality of cells in both hydrogels, while the right and left images of FIG. 17 show higher magnification of selected regions of the middle image, and shows cell and particle arrangements.

The method provided in this example allows for the combination of unique cell/particle arrangements to form multiphasic constructs that more accurately mimic tissues with differences in regional/zonal arrangements.

Example 9

The Effect of Iron Oxide Particles on Mechanical Properties of Hydrogels

Hydrogel mechanical properties were examined after addition of iron oxide particles (NArc and MagN97) into 2% alginate hydrogels. Briefly, 2% alginate gels were crosslinked in $CaCl_2$ with MagN97 particles that were either magnetically aligned into columns or randomly mixed throughout the gel. Table 2 below provides a summary of the results of this study.

Young's Modulus was only significantly increased in gels containing vertically aligned MagN97 at 10 mg/mL (Table 2; $P<0.02$). Conversely, randomly mixed or non-aligned MagN97 particles at 10 mg/mL were significantly less stiff ($P<0.04$). Without wishing to be bound by theory, the decrease in stiffness in the random gels may be due to interference in the crosslinking process with increased particles throughout the gel. Additionally, without wishing to be bound by theory, formation of columns and the creation of particle-free areas allowing normal crosslinking contribute to increased gel stiffness.

Stiffness assessments of gels containing 1 mg/mL of randomly or non-organized particles indicated that gels with NArc particles (Young's modulus (E)=8.4±0.11 KPa) and MagN97 particles (E=7.40±0.71 KPa) were less stiff compared to the control (no particle) gels (E=10.77±1.18 KPa).

Vertical alignment of MagN97 particles led to gels with similar in stiffness (E=10.02±0.82 KPa) compared to the control gels, while vertically aligned NArc gel stiffness (E=8.23±0.39 KPa) remained similar to the non-organized NArc gels. Randomly mixing NArc or MagN97 reduced alginate gel stiffness, while vertically orienting MagN97 restored gel stiffness to control (no particle) levels.

Controlling the concentration and orientation of the particles within the gels provides an additional means of modulating mechanical properties of engineered tissues, particularly in demanding in vivo environments.

TABLE 2

Gel stiffness (Young's Modulus) of 2% alginate gels crosslinked in CaCl₂ with MagN97 particles.

| Condition | MagN97 Content (mg/mL) | Young's Modulus (Mpa) |
|---|---|---|
| Control | 0 | 0.020 ± 0.005 |
| Vertically aligned | 1 | 0.029 ± 0.008 |
|  | 5 | 0.023 ± 0.002 |
|  | 10* | 0.034 ± 0.003 |
| Randomly distributed | 1 | 0.022 ± 0.006 |
|  | 5 | 0.017 ± 0.004 |
|  | 10** | 0.010 ± 0.003 |

T-test comparisons between control and treatment.
*P < 0.02,
**P < 0.004

Example 10

Figure 18:
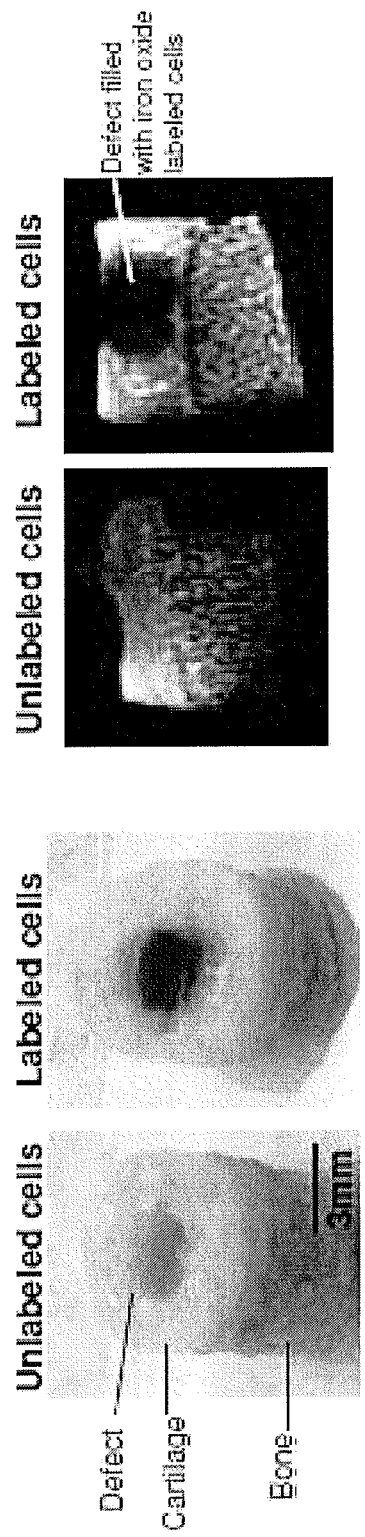
FIG. 18 (left) are images of bovine osteochondral chores with a 3 mm central defect, filled with either MagN97 labeled cells or unlabeled cells.

Organization of Cells in Cartilage Explants Defects Guided by External Magnetic Fields The ease of labeling cells and the ability for remote manipulation provides an opportunity to implant and organize cells directly into the target tissues. Cartilage defects in bovine osteochondral explants were created surgically. Cartilage lesions were repaired with labeled and organized cells in alginate and cultured for 2 weeks (FIG. 18).

Bovine osteochondral cores (6 mm diameter) with a 3 mm central defect were filled with either unlabeled cells or MagN97 labeled cells in alginate ($2 \times 10^6$ cells per defect). Labeled cells were either aligned or nonaligned (FIG. 18). All cores were cultured in ITS+ medium with TGFβ1 (10 ng/mL) for 2 weeks before histological assessment.

Defects filled with MagN97 labeled chondrocytes (FIG. 18, right) demonstrated loss of MRI signal (using 2D fast spin echo (FSE) imaging and 3D ultrashort TE (UTE) sequences) indicative of the presence of iron oxide compared to defects filled without particles. After 2 weeks of culture, repair tissue in labeled treatments was of higher quality and integrated well with the surrounding native tissue (FIG. 18, right).

Optimal cell MagN97 labeling and magnetic field settings indicated that between 1-10 mg of iron oxide was sufficient to label cells in monolayer culture and approximately 500 gauss was needed to reproducibly arrange cells in the defects.

Figure 19:
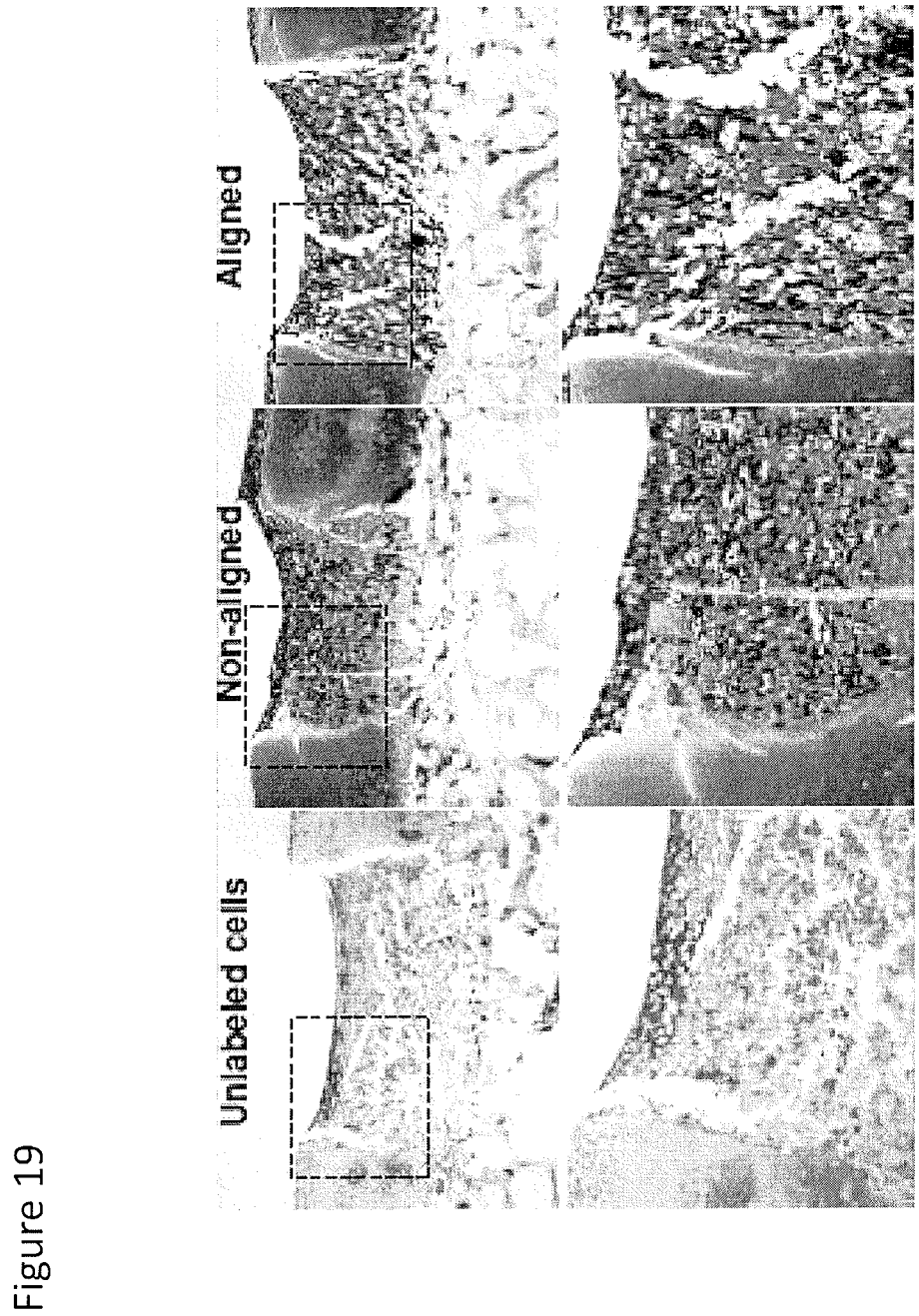
FIGS. 19-21 are optical micrographs showing Alcian blue stained sections of filled defects, where the defects were filed with either unlabeled cells (FIG. 19), labeled and non-magnetically aligned cells (FIGS. 19, 20) or labeled and magnetically aligned cells (FIGS. 19-21).
Figure 20:
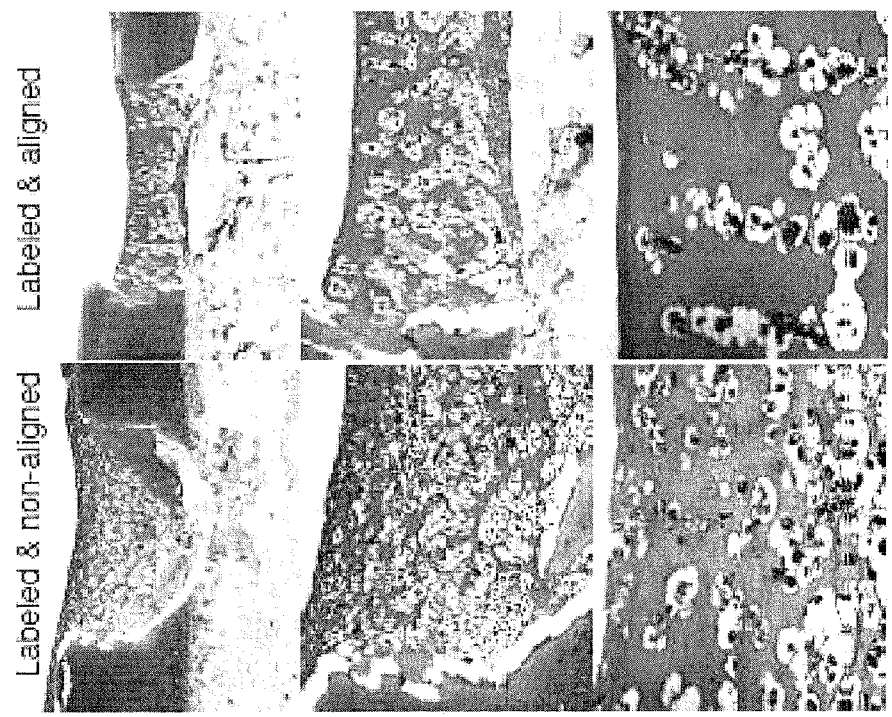
Figure 21:
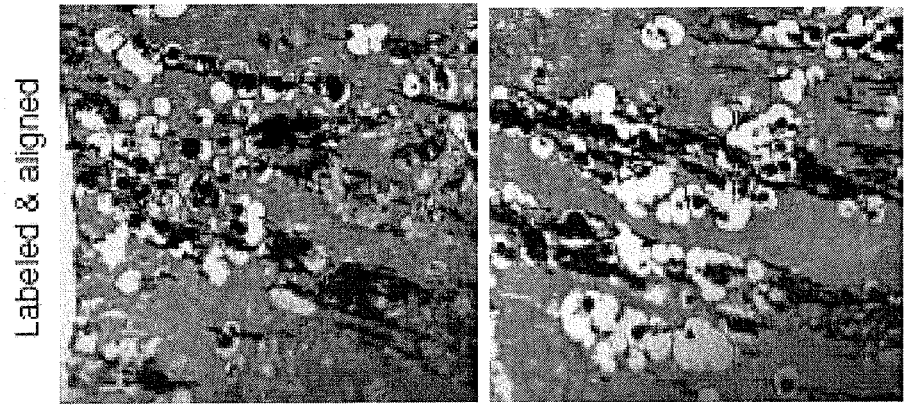

Micrographs of the filled-in defects are provided in FIGS. 19, 20 and 21. Cells were either (1) unlabeled, (2) labeled and non-aligned, or (3) labeled and aligned. FIG. 19 shows a panel of micrographs of sections stained Alcian blue. Upper images (4× magnification) show native cartilage, defect and subchondral bone. Dotted insets (lower images; 10× magnification) show interaction between repair and native tissues for each of the three groups.

FIG. 20 is a micrograph of cells that were optimally labeled (5 mg/mL, MagN97) and subjected to optimal magnetic field settings (>500 gauss) to reproducibly form cell columns. The top images are magnified 4×, the middle images are magnified 10× and the bottom images are magnified 40×.

Another micrograph (40× magnification) of a defect filled with labeled chondrocytes is proved in FIG. 21. In this experiment, chondrocytes wee labeled with 10 mg/mL MagN97. The image shows the cell and particle arrangement.

Example 11

Figure 22:
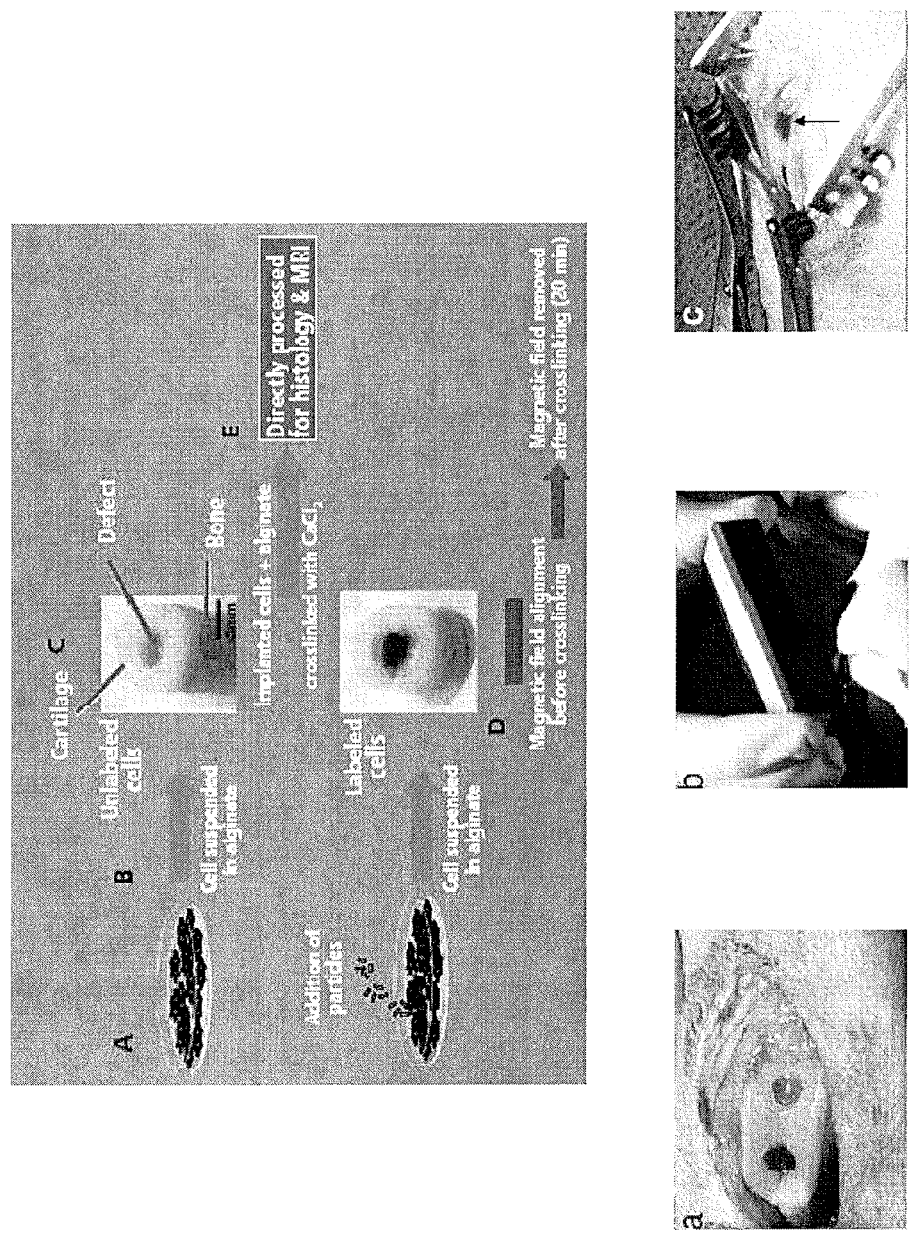
FIG. 22 is a flow chart showing experimental setup of Example 10.
Figure 23:
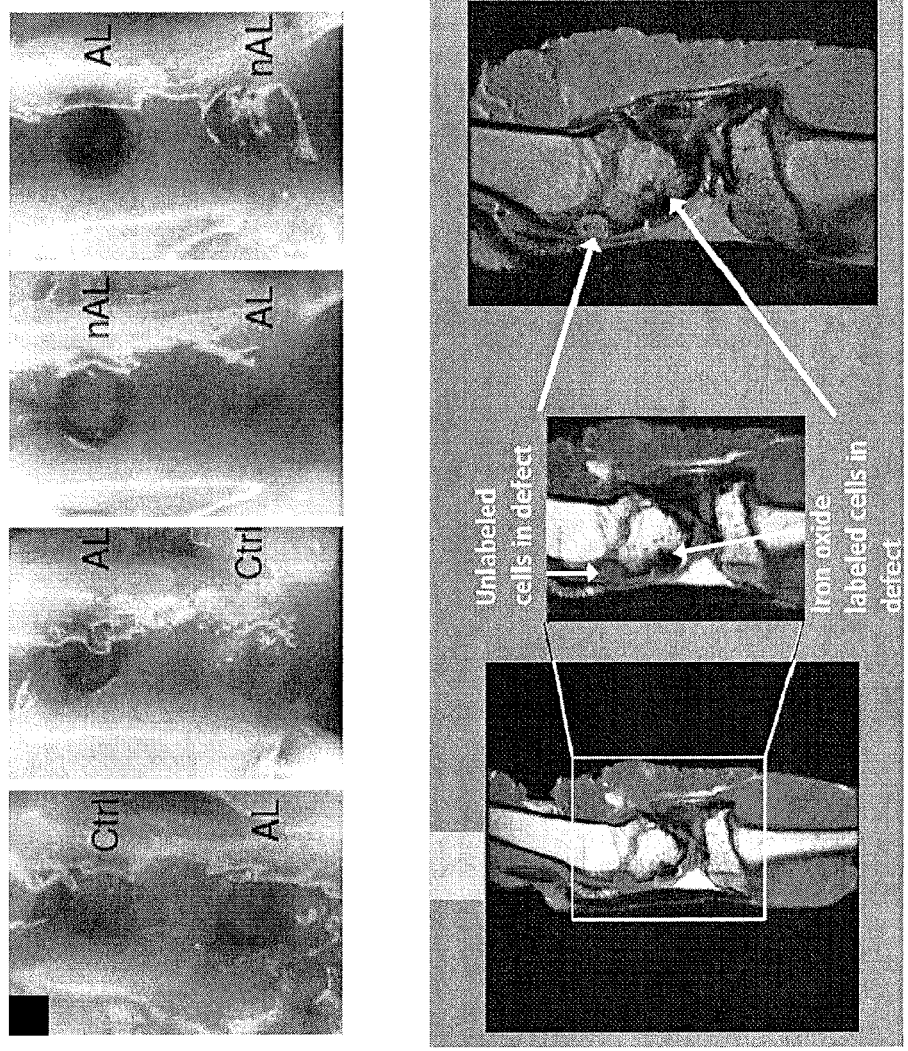
FIG. 23 (top) shows macroscopic images of defects after 4 weeks of cell implantation. The bottom images are MRI images of rabbit knee showing osteochondral defects implanted with either unlabeled or labeled cells. (AL=aligned; nAL=non-aligned, Ctrl=control).

In Vivo Transplantation of MagN97 Labeled Cells in New Zealand White Rabbit Osteochondral Defect Model An in vivo rabbit osteochondral defect model was employed to test implantation and surgical retention in vivo, and to examine whether cells could be tracked in the knee using MRI (FIGS. 21-22). Two osteochondral defects of 3.2 mm (wide) and 2 mm (deep) were surgically created in the trochlear groove of each knee of two 15-week old New Zealand White (NZW) rabbits, with the Scripps Research Institute, IACUC approval, Protocol Number: 09-0132 (FIG. 21, bottom right).

Monolayer cultured NZW rabbit chondrocytes were labeled with either (1) 5 mg/mL MagN97, or (2) maintained unlabeled and suspended in 2% alginate and aseptically transferred into pre-assigned defects. Chondrocytes were exposed to magnetic particles for 12 hours in order to label. Some defects were filled with unlabeled cells (control), other were filled with MagN97 labeled cells that were either aligned (ordered) with an external magnet held above the filled defect (AL) or filled with labeled cells and not aligned (nAL).

The cells were transferred into pre-assigned defects.

The defects filled with MagN97 labeled cells were either aligned with an external magnet (~500 gauss) held above the filled defect or maintained non-aligned (FIG. 21, bottom). Following any alignments, the alginate in each defect was crosslinked with $CaCl_2$. Rabbits were maintained for 4 weeks prior to euthanasia. Implanted rabbit chondrocytes in alginate were retained in all defect sites after 4 weeks (FIG. 22, top). The knees were processed for MRI imaging, macroscopic evaluation, and histological analysis.

Histological assessment indicated extensive remodeling and replacement of the implanted alginate. Sagittal MRI images demonstrated the capacity to locate unlabeled and labeled cells in the rabbit knee (FIG. 22, bottom). A three magnet configuration was found effective for simulating cellular arrangements that mimic articular cartilage zonal architecture (FIG. 15).

FIG. 22 (top) shows the filled defect after the alginate has crosslinked.

After 4 weeks, the implants remained in the defects and macroscopic assessment shows early defect healing (FIG. 22, top). In the images presented in FIG. 22, top, Ctrl=control non-labeled; AL=labeled and magnetically aligned; and nAL=labeled and non-magnetically aligned).

Imaging the knee using MRI clearly identified defects that were either labeled or unlabeled with MagN97 (FIG. 22, bottom).

All, document, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method of forming a magnetic field-organized tissue construct comprising:
    a) mixing a plurality of magnetically labeled cells with a cross-linkable hydrogel to form a cell-hydrogel mixture,
    b) manipulating at least a portion of the plurality of magnetically labeled cells by applying a magnetic field thereto, thereby arranging the magnetically labeled cells into a specific cellular arrangement, and
    c) crosslinking the cross-linkable hydrogel, wherein the crosslinking is provided prior to, during, and/or after said applying of the magnetic field, thereby forming the magnetic field-organized tissue construct.

2. The method of claim 1, further comprising introducing the cell-hydrogel mixture into a tissue defect in a patient.

3. The method of claim 1, further comprising introducing the cell-hydrogel mixture into a cell culture vessel.

4. The method of claim 1, wherein the cross-linkable hydrogel comprises a polymer selected from the group consisting of hyaluronic acid, chondroitin sulfate, collagen, fibrin, chondroitin sulfate (CS), a gelatinous protein mixture secreted by Engelbreth-Hohn Swarm (EHS) mouse sarcoma cells (Matrigel™), alginate, chitosan, fibrin, agarose, silk, and combinations thereof.

5. The method of claim 1, wherein the cross-linkable hydrogel comprises a synthetic polymer selected from the group consisting of polymers and copolymers of ethylene oxide, poly(ethylene oxide), poly(ethylene glycol diacrylate), polymers and copolymers of vinyl alcohol, poly(vinyl alcohol), polymers and copolymers of acrylic or methacrylic acid, poly(acrylic acid), poly(acrylamidomethyl propane sulfonic acid), poly(hydroxyl ethyl methacrylate), poly(propylene fumarate-co-ethylene glycol), and combinations thereof.

6. The method of claim 1, wherein the crosslinking comprises forming ionic cross links.

7. The method of claim 6, wherein the ionic cross links are formed with the addition of a divalent metal ion.

8. The method of claim 1, wherein the crosslinking comprises forming covalent crosslinks.

9. The method of claim 8, wherein the covalent crosslinks are formed thermally or by radiation.

10. The method of claim 9, wherein the covalent crosslinks are formed by UV irradiation or gamma ($\gamma$)-irradiation.

11. The method of claim 1, wherein the plurality of magnetically labeled cells are labeled with iron oxide particles.

12. The method of claim 11, wherein the iron oxide particles are selected from the group consisting of $Fe_2O_3$ and $Fe_3O_4$ particles.

13. The method of claim 1, wherein the plurality of magnetically labeled cells are selected from the group consisting of magnetically labeled chondrocytes, mesenchymal stem cells, embryonic stem cells, keratinocytes, osteoblasts, tenocytes, fibrocytes, endothelial cells, smooth muscle cells, fibroblasts, cardiomyocytes, skeletal myocytes, hepatocytes, alpha cells, beta cells, delta cells, enterocytes, paneth cells, enteroendocrine cells, goblet cells, tuft cells, glomerulus parietal cells, glomerulus podocytes, proximal tubule brush border cells, Loop of Henle thin segment cells, distal renal tubule cells, collecting duct cells, ameloblast epithelial cells, cementocytes, odontocytes, urinary epithelium cells, breast epithelial cells, cuboidal cells, myoepithelial cells, and combinations thereof.

14. The method of claim 1, wherein the plurality of magnetically labeled cells comprise a plurality of cells with one or more magnetic particles adhered to each of the cells.

15. The method claim 1, wherein the plurality of magnetically labeled cells comprise a plurality of cells with one or more magnetic particles within each of the cells.

16. The method of claim 1, wherein the mixing comprises mixing a suspension comprising the plurality of magnetically labeled cells with a solution or suspension of the cross-linkable hydrogel, thereby introducing the magnetically labeled cells into the cross-linkable hydrogel.

17. The method of claim 1, wherein the cross-linkable hydrogel comprises a cross-linking gradient.

18. The method of claim 1, wherein the magnetic field is applied prior to cross-linking the cross-linkable hydrogel.

19. The method of claim 1, wherein the magnetic field is applied a plurality of times before, during or after crosslinking, or a combination thereof.

20. The method of claim 1, wherein one or more magnetic fields are applied or combined to form multiple orientations of the magnetically-labeled cells.

21. The method of claim 20, wherein one or more magnetic fields are applied or combined to form a three-dimensional orientation of the magnetically-labeled cells.

22. The method of claim 1, comprising:
    a) mixing a first plurality of magnetically labeled cells with a first cross-linkable hydrogel to form a first cell-hydrogel mixture;
    b) manipulating at least a portion of the first plurality of magnetically labeled cells by applying a first magnetic field thereto, thereby arranging the first plurality of magnetically labeled cells into a first specific cellular arrangement;
    c) crosslinking the first cross-linkable hydrogel, thereby forming a first magnetic field-organized tissue construct, wherein the crosslinking is provided prior to, during, and/or after said applying of the magnetic field of step (b);
    d) mixing a second plurality of magnetically labeled cells with a second cross-linkable hydrogel to form a second cell-hydrogel mixture;
    e) manipulating at least a portion of the second plurality of magnetically labeled cells by applying a second magnetic field thereto, thereby arranging the second plurality of magnetically labeled cells into a second specific cellular arrangement;
    f) crosslinking the second cross-linkable hydrogel, thereby forming a second magnetic field-organized tissue construct, wherein the crosslinking is provided prior to, during, and/or after said applying of the magnetic field of step (e); and
    g) combining the first and second magnetic field-organized tissue constructs, thereby forming a magnetic field-organized tissue construct having said first and second cellular arrangements.

23. The method of claim 22, wherein the combining in step (g) is in within a tissue defect in a patient.

24. The method of claim 1, wherein a magnet selected from the group consisting of: a barium ferrite magnet, a N45 neodymium magnet, an electromagnet and a Ni—Cu—Ni coated neodymium magnet is used to create the magnetic field.

25. A magnetic field-organized tissue construct formed by a method comprising:
    a) mixing a plurality of magnetically labeled cells with a cross-linkable hydrogel to form a cell-hydrogel mixture,
    b) manipulating at least a portion of the plurality of magnetically labeled cells by applying a magnetic field thereto thereby arranging the magnetically labeled cells into a specific cellular arrangement, and c) crosslinking the cross-linkable hydrogel, wherein the crosslinking is provided prior to, during, and/or after said applying of the magnetic field thereby forming the magnetic field-organized tissue construct.

26. The magnetic field-organized tissue construct of claim 25, wherein the plurality of magnetically labeled cells comprise magnetically labeled chondrocytes.

27. The magnetic field-organized tissue construct of claim 25, wherein the magnetic field-organized cell tissue comprises heart, liver, lung, pancreas or breast cells.

28. The magnetic field-organized tissue construct of claim 25, wherein prior to step (a), the plurality of magnetically labeled cells are grown in a monolayer.

29. The magnetic field-organized tissue construct of claim 28, wherein the plurality of magnetically labeled cells are grown in the monolayer to at least 50% confluence.

30. The magnetic field-organized tissue construct of claim 28, wherein the monolayer comprises at least two cell types.

31. The magnetic field-organized tissue construct of claim 25, wherein the magnetically labelled cells (c*) and hydrogel (h) are present in the construct, by volume thereof, in a c*:h ratio from about 1:10 (v/v) to about 10:1 (v/v).

32. The magnetic field-organized tissue construct of claim 25, wherein the strength of the magnetic field has a strength from about 25 gauss (G) to about 2000 G.

33. A magnetic field-organized tissue construct comprising:
a) magnetically labeled cells; and
b) a crosslinked hydrogel,
wherein the magnetically labeled cells are magnetic field-oriented in the crosslinked hydrogel to form the magnetic field-organized tissue construct.

34. The magnetic field-organized tissue construct of claim 33, wherein the magnetically labeled cells comprise chondrocytes.

35. The magnetic field-organized tissue construct of claim 33, wherein the organized cell tissue comprises heart, liver, lung, kidney or breast cells.

36. The magnetic field-organized tissue construct of claim 33, wherein the magnetically labeled cells comprise magnetic particles selected from the group consisting of: $Fe_2O_3$ particles, $Fe_3O_4$ particles, $CrO_2$ particles, surface coated Co particles, surface coated Ni particles, surface coated Fe particles, surface coated CoPt particles, surface coated CoPd particles, and combinations thereof.

37. The magnetic field-organized tissue construct of claim 33, wherein the magnetically labeled cells comprise magnetic particles having an average diameter in the range of about 15 nm to about 15 μm.

38. The magnetic field-organized tissue construct of claim 37, wherein the magnetically labeled cells comprise magnetic particles having an average diameter in the range of about 20 nm to about 5 μm.

39. The magnetic field-organized tissue construct of claim 38, wherein a first column of a first portion of the magnetically labeled cells is arranged in a first orientation and a second column of a second portion of the magnetically labeled cells is arranged in a second orientation, wherein the first orientation and the second orientation are different.

40. The magnetic field-organized tissue construct of claim 33, wherein at least a portion of the magnetically labeled cells are oriented vertically arranged in one or more columns.

41. The magnetic field-organized tissue construct of claim 40, wherein a first column of a first portion of the magnetically labeled cells is arranged in a first orientation and a second column of a second portion of the magnetically labeled cells is arranged in a second orientation, wherein the first orientation and the second orientation are the same.

42. The magnetic field-organized tissue construct of claim 33, wherein the magnetic field-organized tissue construct comprises at least two crosslinked hydrogels.

43. The magnetic field-organized tissue construct of claim 42, wherein each of the at least two crosslinked hydrogels comprise the same polymer.

44. The magnetic field-organized tissue construct of claim 42, wherein the at least two crosslinked hydrogels comprise at least two different polymers.

45. The magnetic field-organized tissue construct of claim 25 or 33, wherein the magnetic labels are magnetic particles and wherein the mass of the magnetic particles present in a volume of the cell-hydrogel mixture is from about 0.01 mg/mL to about 100 mg/mL.

* * * * *

UNITED STATES PATENT AND TRADEMARK OFFICE
CERTIFICATE OF CORRECTION

| | | |
|---|---|---|
| PATENT NO. | : 9,051,549 B2 | Page 1 of 1 |
| APPLICATION NO. | : 13/402627 | |
| DATED | : June 9, 2015 | |
| INVENTOR(S) | : Grogan et al. | |

It is certified that error appears in the above-identified patent and that said Letters Patent is hereby corrected as shown below:

In the claims

Column 32, line 12, Claim 39 should read as follows:

39. The magnetic field-organized tissue construct of claim 33, wherein at least a portion of the magnetically labeled cells are arranged in one or more columns.

Column 32, line 18, Claim 40 should read as follows:

40. The magnetic field-organized tissue construct of claim 39, wherein a first column of a first portion of the magnetically labeled cells is arranged in a first orientation and a second column of a second portion of the magnetically labeled cells is arranged in a second orientation, wherein the first orientation and the second orientation are different.

Column 32, line 21, Claim 41 should read as follows:

41. The magnetic field-organized tissue construct of claim 39, wherein a first column of a first portion of the magnetically labeled cells is arranged in a first orientation and a second column of a second portion of the magnetically labeled cells is arranged in a second orientation, wherein the first orientation and the second orientation are the same.

Signed and Sealed this
Sixteenth Day of February, 2016

Michelle K. Lee
*Director of the United States Patent and Trademark Office*